US012690831B2

(12) United States Patent
Raveendranath et al.

(10) Patent No.: US 12,690,831 B2
(45) Date of Patent: Jul. 28, 2026

(54) IMAGING PROTOCOL REVIEW MANAGEMENT SYSTEM

(71) Applicant: GE Precision Healthcare LLC, Waukesha, WI (US)

(72) Inventors: Sanoj Raveendranath, Bangalore (IN); Jithashree R, Bangalore (IN); Sushmita Kari, Bangalore (IN); Yaxi Shen, Waukesha, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 173 days.

(21) Appl. No.: 18/713,144

(22) PCT Filed: Nov. 23, 2022

(86) PCT No.: PCT/US2022/050919
§ 371 (c)(1),
(2) Date: May 23, 2024

(87) PCT Pub. No.: WO2023/097011
PCT Pub. Date: Jun. 1, 2023

(65) Prior Publication Data
US 2025/0017547 A1     Jan. 16, 2025

(30) Foreign Application Priority Data

Nov. 24, 2021     (IN) .............................. 202141054228

(51) Int. Cl.
*A61B 6/00*          (2024.01)
*A61B 6/03*          (2006.01)
(52) U.S. Cl.
CPC .............. *A61B 6/542* (2013.01); *A61B 6/563* (2013.01); *A61B 6/032* (2013.01)

(58) Field of Classification Search
CPC ......... A61B 6/563; A61B 6/542; A61B 6/032; A61B 8/54; A61B 8/565; A61B 6/037;
(Continued)

(56) References Cited

U.S. PATENT DOCUMENTS

2008/0119717 A1     5/2008  Profio
2018/0032675 A1     2/2018  Dominick
(Continued)

FOREIGN PATENT DOCUMENTS

WO        2018098311 W      5/2018

OTHER PUBLICATIONS

EP application 22899393.7 filed May 6, 2024—extended Search Report issued Aug. 20, 2025; 10 pages.
(Continued)

*Primary Examiner* — Irakli Kiknadze

(57)                ABSTRACT
A system and method for reviewing imaging protocols in an imaging protocol management system is described herein. An example system includes processors and storage devices in a cloud and a cloud-based imaging protocol manager leveraging the processors and the storage devices. The imaging protocol manager includes a library for storing imaging protocols and a review module configured to review and standardize the imaging protocols stored in the library. The system also includes a user interface device having a web browser-based application to access imaging protocols stored in the library. The web browser-based application enables creation, editing, and review of the imaging protocols stored in the library. The imaging protocols are approved using the web browser-based application prior to being published in the library, and a plurality of imaging systems. The plurality of imaging systems accesses the imaging protocols from the library.

20 Claims, 21 Drawing Sheets

(58) Field of Classification Search

CPC ........... A61B 6/545; A61B 6/02; A61B 6/581;
A61B 6/566; A61B 5/055; A61B 5/0035;
A61B 6/5205; A61B 6/54; G16H 40/67;
G16H 30/20; G16H 40/40; G16H 40/63;
G16H 40/20; G16H 10/60; H04L 12/12;
H04L 67/60; H04L 67/12; H04L 67/34;
H04L 67/10; H04L 63/08; H04L 67/55;
H04L 67/02; H04L 41/0846; H04L
67/125; H04L 41/0806; H04L 41/0894;
H04L 41/22; H04L 67/26; H04L 67/32;
G06F 8/60; G06F 16/289; G06F 16/951;
G06F 21/31; G06F 21/84; G06F 9/542;
G01R 33/543; G01N 23/04; H04N
23/617; H04N 23/661; H04N 5/23206;
H04N 5/23225

USPC ......................................................... 378/91

See application file for complete search history.

(56) References Cited

U.S. PATENT DOCUMENTS

2018/0144823 A1\*  5/2018  Raman ................... A61B 6/545
2020/0222020 A1     7/2020  Raman

OTHER PUBLICATIONS

International Application No. PCT/US2022/050919 filed Nov. 23, 2022—International Search Report and Written Opinion issued on Feb. 24, 2023; 12 pages.

\* cited by examiner

600

Create new review                                      X

Reviewers

Review group name       Frequency
Ped_head ▼              default(365 days) ▼    ( change it to 90 days )

Protocol

402 — ☐ ~~~ ~~~ ~~~ ~~ ~~~

☑ ~~~ ~~~ ~~~ ~~ ~~~

☑ ~~~ ~~~ ~~~ ~~ ~~~

Done

Review                              Create new group  X

[ show all | assigned to me ]

Review group name    Model
Ped Head ▼           Rev_12343ddvfv ▼                ⋮ — 704

| Protocol | Review Status | Last Modified | Due Date | CT2 | CT3 | CT4 | CT5 |
|----------|---------------|---------------|----------|-----|-----|-----|-----|
| ☐ ~~~ | Not Reviewed | - | - | | | ○ | |
| ☐ ~~~ | Not Reviewed | - | - | | | | |
| ☐ ~~~ | Not Reviewed | - | - | | | | |
| ☐ ~~~ | Not Reviewed | - | - | | | | |
| ☐ ~~~ | Not Reviewed | - | - | ○ | | | ○ |

402

○ Deviated

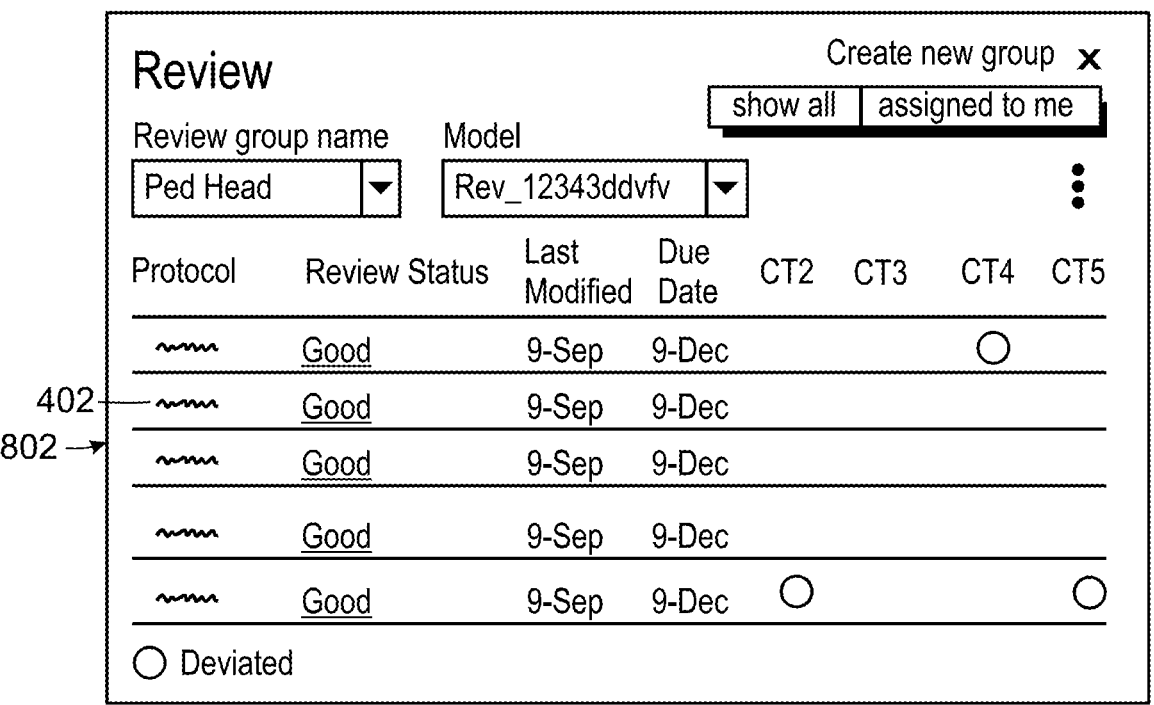

FIG. 10

| Review group name | Model | | | | | | | |
|---|---|---|---|---|---|---|---|---|
| Ped Head ▼ | Rev_12343ddvfv ▼ | | | | | | | ⋮ |
| Protocol | Review Status | Last Modified | Due Date | CT2 | CT3 | CT4 | CT5 |
| ∿ | Good | 9-Sep | 9-Dec | | | ○ | |
| ∿ | Good | 9-Sep | 9-Dec | | | | |
| ∿ | Good | 9-Sep | 9-Dec | | | | |
| ∿ | Good | 9-Sep | 9-Dec | | | | |
| ∿ | Good | 9-Sep | 9-Dec | ○ | | | ○ |

Review — Create new group ✗ — show all | assigned to me

○ Deviated

---

Review — Create new group ✗ — show all | assigned to me

| Review group name | Model | | | | | | | |
|---|---|---|---|---|---|---|---|---|
| Ped Head ▼ | Rev_12343ddvfv ▼ | | | | | | | ⋮ |
| Protocol | Review Status | Last Modified | Due Date | CT2 | CT3 | CT4 | CT5 |
| ∿ | Due soon | 9-Sep | 9-Dec | | | ○ | |
| ∿ | Due soon | 9-Sep | 9-Dec | | | | |
| ∿ | Due soon | 9-Sep | 9-Dec | | | | |
| ∿ | Due soon | 9-Sep | 9-Dec | | | | |
| ∿ | Due soon | 9-Sep | 9-Dec | ○ | | | ○ |

○ Deviated

FIG. 11

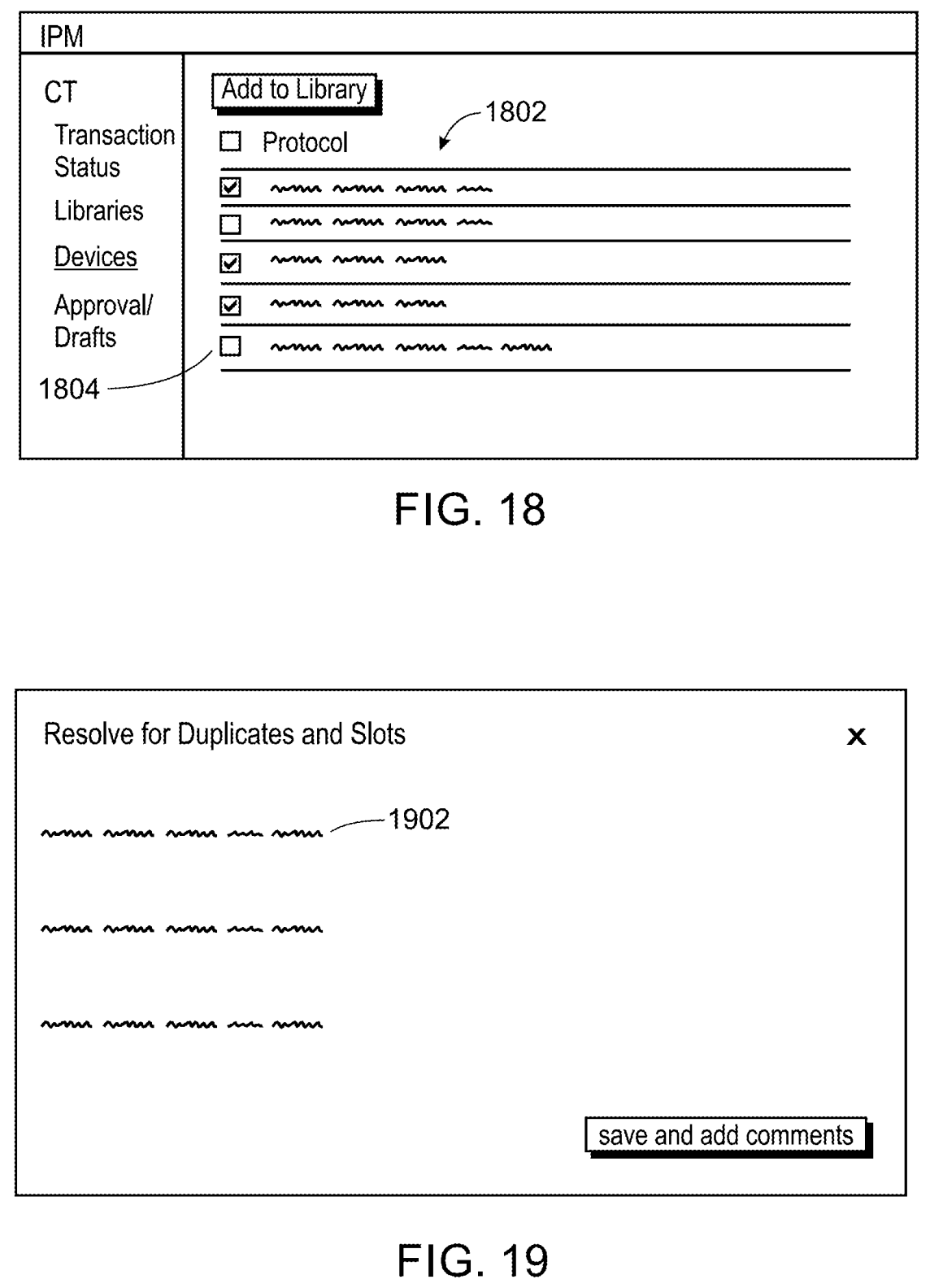

IPM

CT

Transaction
Status

Libraries

Devices

Approval/
Drafts

1804 ─

Add to Library

☐ Protocol          ╱─1802

Resolve for Duplicates and Slots                    ✕

～～ ～～ ～～ ～ ～～ ─1902

～～ ～～ ～～ ～ ～～

～～ ～～ ～～ ～ ～～ save and add comments

FIG. 19

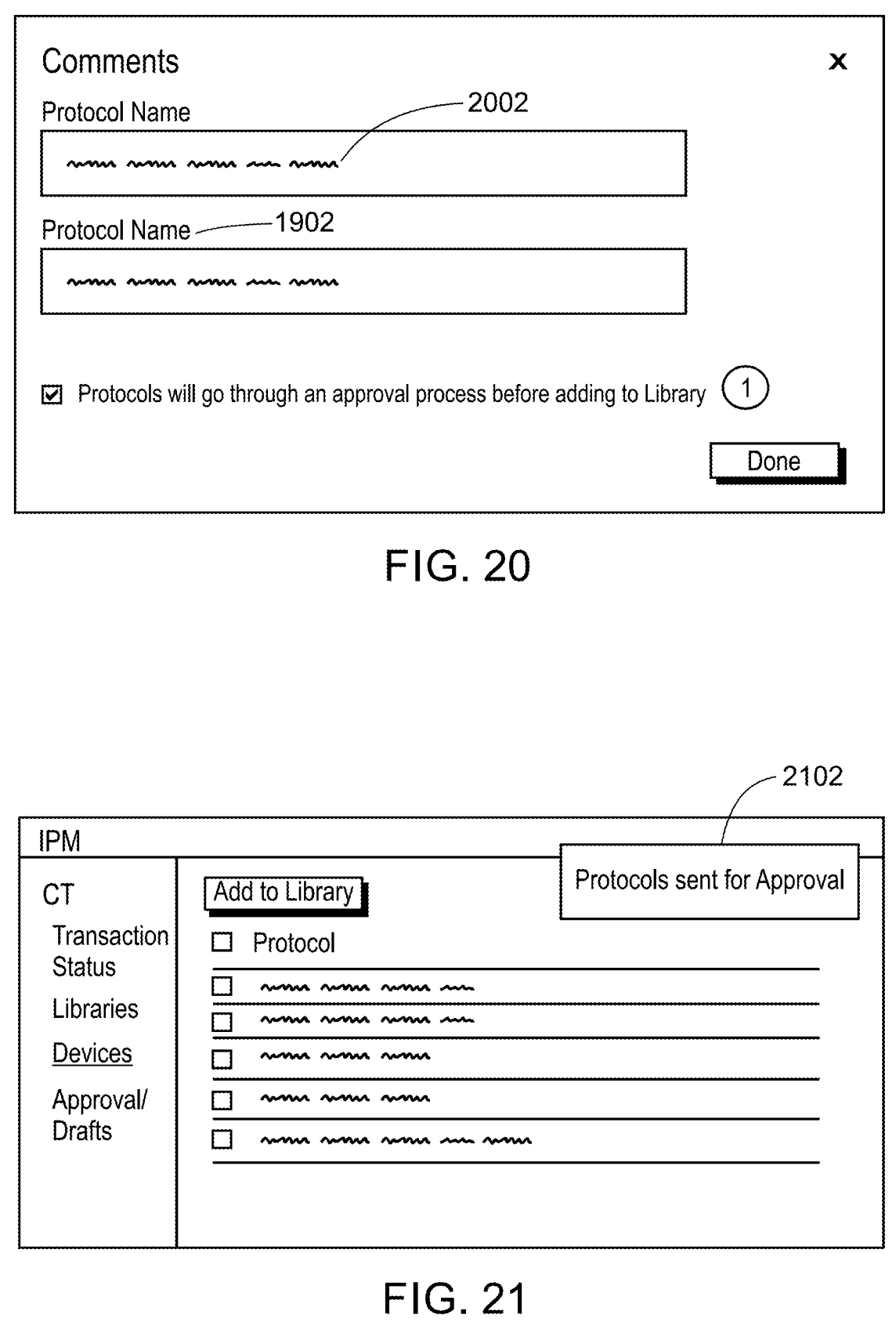

Comments      x

Protocol Name    2002

Protocol Name    1902

☑ Protocols will go through an approval process before adding to Library    ①

Done

IPM

CT

Transaction Status

Libraries

Devices

Approval/ Drafts

Add to Library

☐ Protocol

☐ ~~~~ ~~~~ ~~~~ ~~

☐ ~~~~ ~~~~ ~~~~ ~~

☐ ~~~~ ~~~~ ~~~~

☐ ~~~~ ~~~~ ~~~~

☐ ~~~~ ~~~~ ~~~~ ~~ ~~~~

Protocols sent for Approval

FIG. 21

Figures 22, 23:
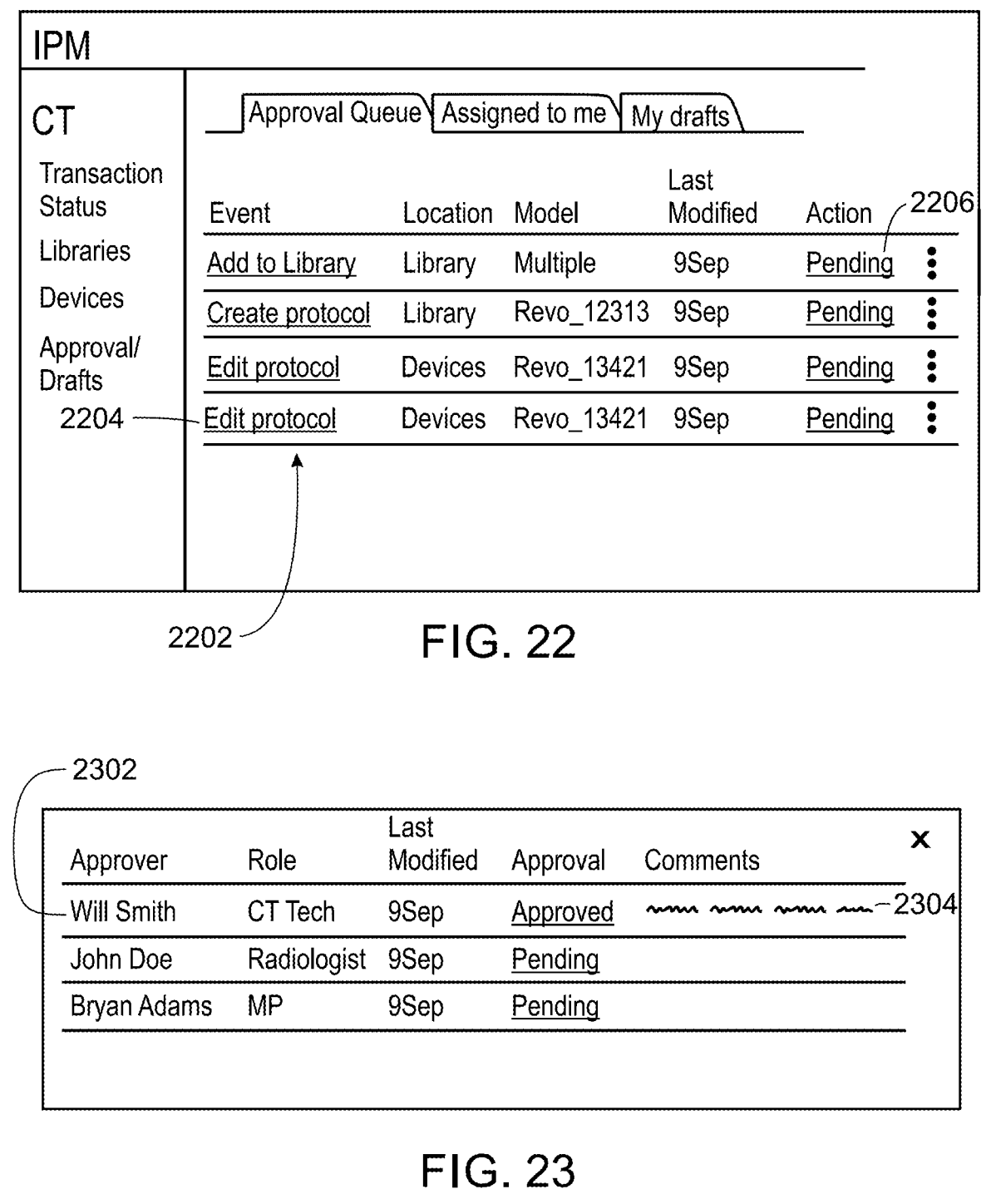

IPM

CT

Transaction
Status

Libraries

Devices

Approval/
Drafts

| | Approval Queue | Assigned to me | My drafts | | | |
|---|---|---|---|---|---|---|
| Event | Location | Model | Last Modified | Action | 2206 | |
| Add to Library | Library | Multiple | 9Sep | Pending | ⋮ | |
| Create protocol | Library | Revo_12313 | 9Sep | Pending | ⋮ | |
| Edit protocol | Devices | Revo_13421 | 9Sep | Pending | ⋮ | |
| Edit protocol | Devices | Revo_13421 | 9Sep | Pending | ⋮ | |

| Approver | Role | Last Modified | Approval | Comments | x |
|---|---|---|---|---|---|
| Will Smith | CT Tech | 9Sep | Approved | ~~~~ ~~~~ ~~~~ ~~ | 2304 |
| John Doe | Radiologist | 9Sep | Pending | | |
| Bryan Adams | MP | 9Sep | Pending | | |

Add to Library (10)     x

Resolve Duplicates | Resolve Slots

✔ Protocol in 2.1 device found in 2.5 in Library

Deviated   2.1 CT Abdomen Angio     renamed as CT Abd Angio in slot 2.2

Comments

✔ Protocol in 2.1 device found in 2.5 in Library

Deviated   2.1 CT Abdomen Angio     renamed as CT Abd Angio in slot 2.2

Comments

See comments

FIG. 24

IPM

CT

Transaction Status

Libraries

Devices

Approval/ Drafts

Approval Queue | Assigned to me | My drafts

2502

| Event | Location | Model | Last Modified | Action |
|---|---|---|---|---|
| Add to Library | Library | Multiple | 9Sep | Rejected |
| Create protocol | Library | Revo_12313 | 9Sep | Pending |
| Edit protocol | Devices | Revo_13421 | 9Sep | Pending |
| Edit protocol | Devices | Revo_13421 | 9Sep | Pending |

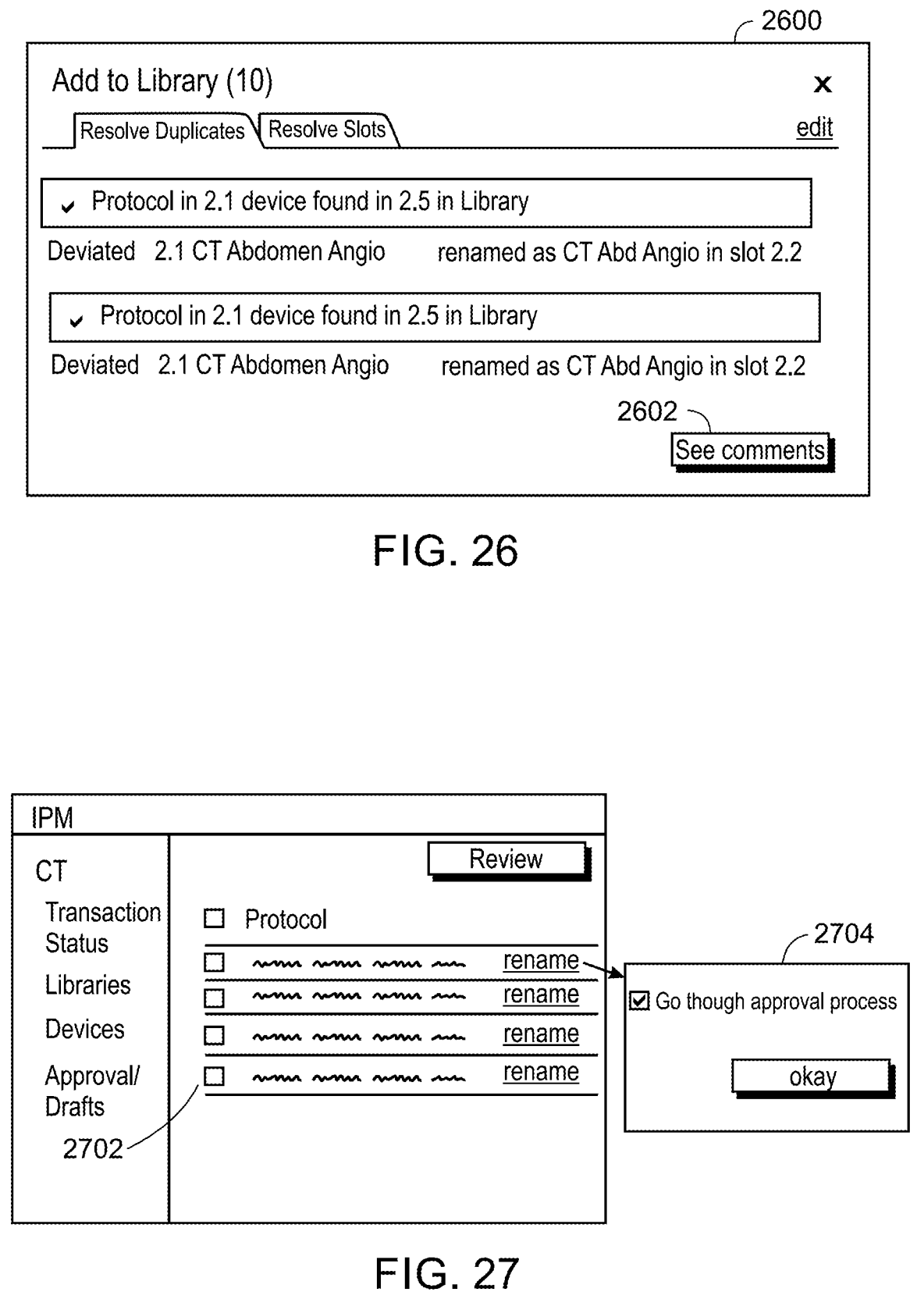

Add to Library (10)                                                    x

Resolve Duplicates    Resolve Slots                                    edit

✔ Protocol in 2.1 device found in 2.5 in Library

Deviated   2.1 CT Abdomen Angio      renamed as CT Abd Angio in slot 2.2

✔ Protocol in 2.1 device found in 2.5 in Library

Deviated   2.1 CT Abdomen Angio      renamed as CT Abd Angio in slot 2.2

2602

See comments

FIG. 26

IPM

CT

Transaction
Status                 ☐ Protocol

Libraries              ☐  ∼∼∼ ∼∼∼ ∼∼∼ ∼∼    rename

Devices                ☐  ∼∼∼ ∼∼∼ ∼∼∼ ∼∼    rename

Approval/              ☐  ∼∼∼ ∼∼∼ ∼∼∼ ∼∼    rename
Drafts
                       ☐  ∼∼∼ ∼∼∼ ∼∼∼ ∼∼    rename
2702

Review

2704

☑ Go though approval process okay

FIG. 27

Figures 28, 29:
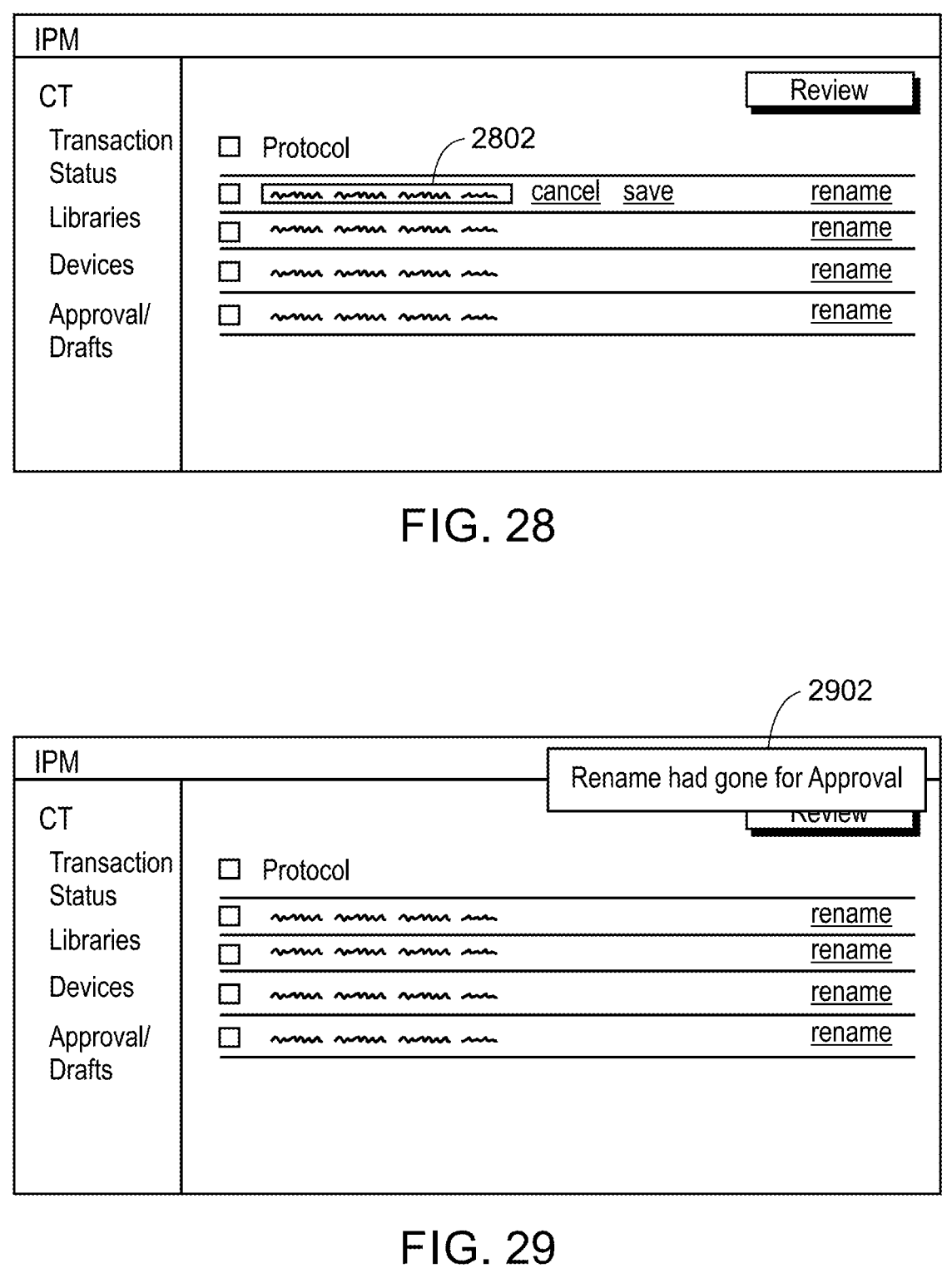

IPM

CT

Transaction Status

Libraries

Devices

Approval/ Drafts

Review

☐ Protocol　　　　　2802

☐ [~~~~ ~~~~ ~~~~ ~~]　cancel　save　　　rename

☐ ~~~~ ~~~~ ~~~~ ~~　　　　　　　　　rename

☐ ~~~~ ~~~~ ~~~~ ~~　　　　　　　　　rename

☐ ~~~~ ~~~~ ~~~~ ~~　　　　　　　　　rename

IPM

CT

Transaction Status

Libraries

Devices

Approval/ Drafts

Rename had gone for Approval

Review

☐ Protocol

☐ ~~~~ ~~~~ ~~~~ ~~　　　　　　　　　rename

☐ ~~~~ ~~~~ ~~~~ ~~　　　　　　　　　rename

☐ ~~~~ ~~~~ ~~~~ ~~　　　　　　　　　rename

☐ ~~~~ ~~~~ ~~~~ ~~　　　　　　　　　rename

IPM

CT

Transaction Status

Libraries

Devices

Approval/ Drafts

| | Approval Queue | Assigned to me | My drafts | | | |
|---|---|---|---|---|---|---|
| | | | | | | Manage Approvers 3002 |
| Event | Location | Model | Last Modified | Approval Status | Action | |
| Edit protocol | Library | Revo_12345 | 9Sep | Not started | Send for Approval | ••• |
| Create protocol | Library | Revo_12313 | 9Sep | Not started | Send for Approval | ••• |
| Edit protocol | Devices | Revo_13421 | 9Sep | Not started | Send for Approval | ••• |
| Edit protocol | Devices | Revo_13421 | 9Sep | Not started | Send for Approval | ••• |

FIG. 30

IMAGING PROTOCOL REVIEW MANAGEMENT SYSTEM

CROSS REFERENCE TO RELATED APPLICATIONS

The present application claims the benefit of Indian Provisional Patent Application No. 202141054228, filed Nov. 24, 2021, and claims priority to PCT Patent Application No. PCT/US2022/050919, which are both incorporated herein by reference.

BACKGROUND

Imaging devices (e.g., magnetic resonance (MR) scanner, computed tomography (CT) scanner, X-ray acquisition system, positron emission tomography (PET) scanner, single-photon emission computed tomography (SPECT) scanner, nuclear medicine (NM) scanner, and combinations thereof (e.g., multi-modality imaging systems, such as PET/CT, PET/MR or SPECT/CT imaging systems, etc.)) use imaging procedures to obtain image data of a target, such as a patient. An imaging procedure is associated with one or more imaging protocols that define image acquiring and/or processing actions or elements, such as one or more imaging parameters, one or more scanning planes in which image(s) are to be captured, and so on. For example, an imaging protocol may include parameters for an imaging device, such as tube current, tube voltage, filter usage, filter type, scan speed, etc. An imaging protocol may define a scanning plane for the associated imaging procedure, specify position and orientation of anatomical structure(s) or region(s) of interest in the patient, etc. An imaging protocol may further specify limits and/or other guidance on image noise, spatial resolution, and image texture including edge sharpness, artifacts, and radiation dose.

An imaging device maintains a protocol database which stores various imaging procedures and/or protocols for the device to use according to one or more scenarios, reasons for examination, etc. The scenarios for examination may include patient size, anatomy type (e.g., heart, lung, kidney, brain, etc.), position, task, etc. For example, imaging protocols can be constructed for particular clinical tasks. A task function such as tumor detection, tumor sizing, vessel sizing, etc., can be incorporated into an objective function to determine a dose distribution for a given task and to find a minimum possible dose for a given performance level. During protocol development, results from similar clinical tasks (e.g., tuning for a given anatomical location, etc.) can be used to inform initial parameter selection for another clinical task (e.g., bone imaging in the wrist may be used to inform the initial selection of parameters for bone imaging in the ankle, etc.).

Imaging procedure and associated imaging protocol(s) can be visualized via a graphical user interface (GUI) for a user (e.g., radiologist, technician, clinical specialist or other healthcare professional) to select. For example, an interactive user interface can include menu and control options to allow the user to select and configure an imaging protocol. For an X-ray imaging protocol for example, the interface allows the user to select an acquisition trajectory, manage radiation dose in real-time, control tube angular orientation, tube tilt, tube position, table motion and/or orientation and other parameters for imaging during reference and/or tomosynthesis scans. When the user selects the imaging protocol via the interface, an imaging procedure associated with the imaging protocol will be performed.

For an organization (e.g., hospital, clinic or other healthcare facility) that has a large fleet of imaging devices at various facilities, managing protocols for the devices can be very costly and time-consuming. Exam quality may be inconsistent due to inconsistent protocols used across the facilities, which may put patient safety and outcome at risk. Compliance with regulations and accreditation requirements may be challenging due to variability in dose, exam duration, and diagnostics quality. In addition, protocols need to be reviewed and kept current all the time. However, modification of protocols may be inefficient because protocols are modified per exam, which results in loss of productivity and revenue. An imaging protocol management system and method with improved efficiency and outcome are generally desired.

Further, the activities involved in reviewing the content of a protocol, and ensuring the correct content is programmed on a scanner or imaging system may be conducted offline if a protocol management system is available, either in hard copy or electronic format in the instance when there is no protocol management system available at a healthcare institution or enterprise system. The review process may become very cumbersome and may be conducted manually in many institutions. The protocols need to be reviewed and verified on each individual scanner or imaging system. A large volume of protocols makes a manual review process labor intensive, error prone and costly. An automatic protocol review management system on an existing imaging protocol manager application is proposed to make the protocol review process easy and automated.

BRIEF SUMMARY

In an aspect, a system for imaging protocol management is described. The system includes one or more processors and one or more storage devices in a cloud and a cloud-based imaging protocol manager leveraging the one or more processors and the one or more storage devices. The imaging protocol manager includes a library storing imaging protocols and a review module configured to review and standardize the imaging protocols stored in the library. The system also includes a user interface device includes a web browser-based application to access imaging protocols stored in the library, the web browser-based application to enable creation, editing, and review of the imaging protocols stored in the library, wherein the imaging protocols are approved using the web browser-based application prior to being published in the library, and a plurality of imaging systems, wherein the plurality of imaging systems accesses the imaging protocols from the library.

In another aspect, a method of managing imaging protocols in an imaging protocol manager is described. The method includes storing imaging protocols in the cloud, acquiring machine-specific details in a standard imaging protocol format, reviewing imaging protocols, via a review module, in a web browser-based application, and uploading imaging protocols to a cloud-based imaging protocol manager, updating imaging systems with the uploaded imaging protocols.

In another aspect, a system for imaging protocol management is described. The system includes one or more processors and one or more storage devices in a cloud and a cloud-based imaging protocol manager leveraging the one or more processors and the one or more storage devices. The imaging protocol manager includes a library storing imaging protocols, a review module configured to review and standardize the imaging protocols stored in the library, and an editing module configured to edit the imaging protocols stored in the library. The system also includes a user interface device includes a web browser-based application to access imaging protocols stored in the library, the web browser-based application to enable creation, editing, and review of the imaging protocols stored in the library, wherein the imaging protocols are approved using the web browser-based application prior to being published in the library, and a plurality of imaging systems, wherein the plurality of imaging systems accesses the imaging protocols from the library.

In yet another aspect, a method of managing imaging protocols in an imaging protocol manager is described. The method includes storing imaging protocols in the cloud, acquiring machine-specific details in a standard imaging protocol format, reviewing imaging protocols, via a review module, in a web browser-based application, editing imaging protocols, via an editing module, in a web browser-based application, and uploading imaging protocols to a cloud-based imaging protocol manager, updating imaging systems with the uploaded imaging protocols.

BRIEF DESCRIPTION OF THE DRAWINGS

Various aspects of this disclosure may be better understood upon reading the following detailed description and upon reference to the drawings in which:

FIGS. 4-13 illustrate example embodiments of a review process of the imaging protocol manager.

FIGS. 18-26 illustrate example embodiments of a process to add a protocol to the imaging protocol manager.

FIGS. 27-29 illustrate example embodiments of a process rename a protocol in the imaging protocol manager.

FIGS. 30-31 illustrate example embodiments of a process to manage approvers of the imaging protocol manager.

Figure 1:
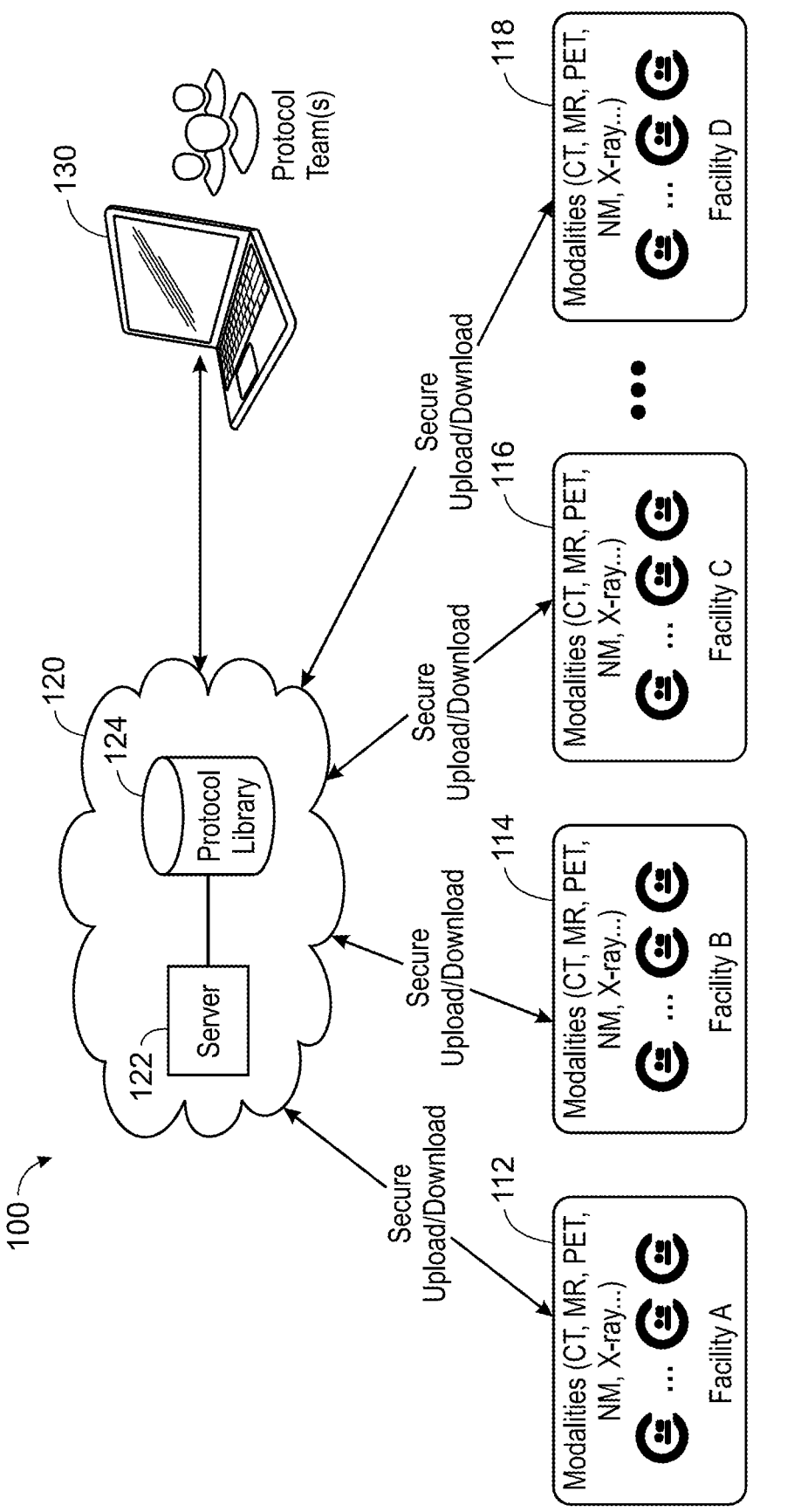
FIG. 1 is a schematic diagram of a system in which an imaging protocol manager is used, in accordance with an exemplary embodiment.

The drawings illustrate specific aspects of the described components, systems and methods for providing photo-therapy treatment. Together with the following description, the drawings demonstrate and explain the principles of the structures, methods, and principles described herein. In the drawings, the thickness and size of components may be exaggerated or otherwise modified for clarity. Well-known structures, materials, or operations are not shown or described in detail to avoid obscuring aspects of the described components, systems and methods.

DETAILED DESCRIPTION

One or more specific embodiments of the present disclosure are described below in order to provide a thorough understanding. These described embodiments are only examples of the systems and methods for managing imaging protocols. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

In addition, it should be understood that references to "one embodiment" or "an embodiment" of the present disclosure are not intended to be interpreted as excluding the existence of additional embodiments that also incorporate the recited features.

Referring to the figures generally, the present disclosure is to provide systems and methods for managing imaging protocols for a fleet of imaging devices. An example imaging protocol management system includes a cloud-based protocol manager that manages imaging protocols across multiple modalities. The example imaging protocol management system is a multi-modality application that provides a web-based user interface that allows the users to view and edit imaging protocols, and the users can remotely view imaging protocols in the imaging system, organize a standard set of imaging protocols in libraries, and distribute the imaging protocols back to the imaging systems. Protocol team(s) such as radiologist, technicians, clinicians, and researchers, can access the protocol manager from a web browser of a computing device (e.g., workstation, computer, laptop) to view and edit protocols stored in a protocol library, which is accessible to all imaging systems. Any user device with a web browser may be capable of accessing the web browser-based application for the image protocol management. The protocol manager can distribute (i.e., push) protocols in the library to applicable imaging devices in the fleet. The protocol manager also tracks and monitors deviation between protocols used by devices and standard protocols in the cloud library.

Via the cloud-based library, the protocol manager facilitates remote pull and push of protocols, which eliminates the need for manually updating protocols on a plurality of imaging devices and thereby eliminating significant time waste. In this way, the protocol manager helps healthcare providers deliver right imaging protocols for each patient with consistency and accuracy over time, which satisfies regulatory and accreditation requirements and governance for imaging protocols. Thus, variability in protocols and image quality can be reduced, and patient safety and consistency of care can be improved. Operational efficiency can be improved by standardizing workflow and procedures across multiple facilities and locations via a centralized protocol library. An effective protocol management process can be established using the protocol manager, insights, and education across the enterprise. Because the protocols are reviewed, edited, and approved via a web browser-based application, the imaging systems are not affected by the review process, and the services provided by the imaging systems are not interrupted. That is, there is no down time for the imaging systems during the protocol review.

Examples described herein include an imaging protocol review management system on the existing Imaging Protocol Manager software application. This review system makes the imaging protocol review process easy and automated. The IPM is a cloud-based multi-modality application used to store and manage imaging system protocols within an enterprise. The IPM application provides a web-based user interface, and the users can remotely view the imaging protocols in the imaging system, organize a standard set of imaging protocols in libraries and distribute the imaging protocols back to the imaging systems.

An imaging protocol management system includes a web-based multi-modality protocol manager that helps identify protocol variation, standardize imaging workflow, and improve protocol compliance to achieve patient safety, operational efficiency, and optimize patient experience, for example. Prior solutions subjected customers to inconsistent exam quality and patient experience across facilities, resulting in loss of productivity (e.g., repeated exams, etc.), referrals, and challenges in meeting regulatory and accreditation requirements, for example. Instead, certain examples disclosed herein provide a web-based protocol management system that helps providers deliver the right image for each patient with consistency and accuracy over time, while satisfying regulatory and accreditation requirements and governance for protocols on imaging devices.

For example, patient outcomes can be improved by reducing variability in protocols and image quality to improve patient safety and consistency of care. Certain examples manage compliance by meeting protocol management regulatory and industry guidelines, as well as improve compliance with clinical standards. Operational efficiency can be improved by standardizing workflow/procedures across multiple facilities and locations via a centralized protocol library, for example. Certain examples facilitate culture change by establishing an effective protocol management process using a protocol manager, insights, and education across the enterprise.

Imaging protocol management and review are essential activities in ensuring patient safety. Several states' regulatory and accreditation groups, such as the American College of Radiology (ACR) CT Accreditation program, have identified imaging protocol management and review as essential activities.

The activities involved in protocol management are reviewing the content of the imaging protocol and ensuring that the right content is programmed on the scanner or imaging system. Reviewing the content of the imaging protocol can be conducted offline if an imaging protocol system (or protocol book) is available, either in hard copy or electronic format in case there is no imaging protocol management solution in a healthcare facility. This becomes very cumbersome and is conducted manually on paper in many healthcare facilities. Ensuring that the right content is programmed on the scanner or imaging system needs to be checked on each individual scanner or imaging system. A large volume of imaging protocols makes manual review labor-intensive, error-prone, and costly.

Through this disclosure we describe an imaging protocol review management system on the existing Imaging Protocol Manager software application. This review system makes the imaging protocol review process easy and automated. The IPM is a cloud-based software application used to store and manage the scanner or imaging system prescription protocols within an enterprise. The IPM software application provides a web-based user interface and the users can remotely view the imaging protocols in the scanners or imaging systems, organize the standard set of imaging protocols in libraries and distribute it back to the scanners or imaging systems. Thus, the users do not need to access or interfere with the imaging systems to review and organize the protocols.

As will be described further below, certain examples can integrate with and operate in a variety of healthcare environments and impact a variety of healthcare scenarios and data through sensing, decision support, workflow management, and control. The following section provides some context and example environment for the presently disclosed technology described further in the subsequent section below.

Referring to FIG. 1, a schematic diagram of a system 100 where an imaging protocol manager is used is shown, in accordance with certain examples. As illustrated in FIG. 1, the system 100 includes a plurality of scanning devices 112, 114, 116, and 118 of various modalities (e.g., CT, MR, PET, NM, X-ray, etc.) located at various facilities A, B, C, and D. In some examples, the facilities A, B, C, and D are operated by one organization (e.g., hospital, clinic). A cloud-based imaging protocol manager 120 leverages one or more server 122 and one or more database 124 connected by network (i.e., in the cloud). A protocol library is stored in the database 124. Structure of the imaging protocol manager 120 will be discussed below in detail with reference to FIG. 2.

Imaging devices 112-118 are communicably connected to the imaging protocol manager 120 via network. Communication between the imaging devices 112-118 and the protocol manager 120 is secure. In some examples, one or more of the imaging devices 112-118 are connected directly to the cloud. In particular, a cloud agent (e.g., client-side application) runs on an imaging device and talks to the protocol manager (e.g., a server-side application) in the cloud.

Imaging devices 112-118 can be registered with the imaging protocol manger 120. Each imaging device can maintain a protocol database which stores protocols used by the device for various scenarios and tasks. After registration, protocols can be imported (i.e., pulled) from the imaging devices 112-118 and stored in the database 124 in the cloud. One or more protocol team(s) (e.g., radiologist, physician, technician, researcher) can access the imaging protocol manager 120 from a user device 130, which can be, for example, a workstation, computer, laptop, or other processing device. In some embodiments, the imaging protocol manger 120 supports a web-based portal or web-based application for the protocol team(s) to access from the user device 130. The web browser-based application can be accessed from any user device with a web browser, enabling easier remote management of the protocols in the image protocol manager. In further embodiments, a browser-based interface can serve as a zero footprint, zero download, and/or other universal viewer for the user device 130. The protocol team(s) can view, edit, and evaluate the protocols through the web-based portal or application. The user interface of the web-based portal/application may be configured to help or guide a user in accessing data and/or functions to facilitate protocol management. In some embodiments, the user interface may be configured according to certain rules, preferences, and/or functions. Furthermore, a user can customize the interface according to his/her desires, preferences, and/or requirements.

The imaging protocol manager 120 can compare protocols pulled from the imaging devices 112-118 to standard protocols published in the protocol library 124 and track any deviations. The protocol manager 120 can also distribute (e.g., push) the published protocols to applicable imaging devices.

Figure 2:
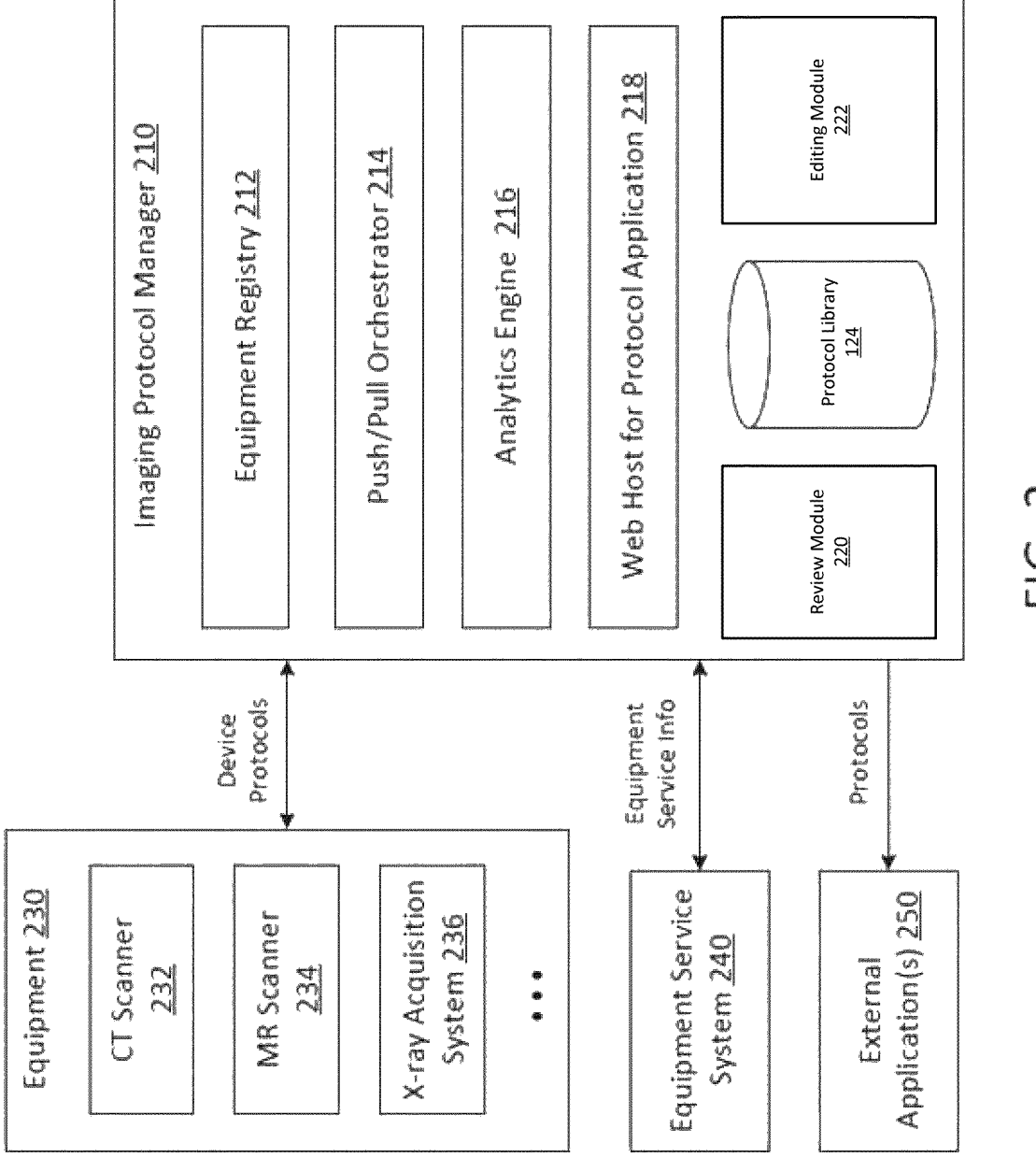
FIG. 2 is a block diagram of an imaging protocol manager in operation, in accordance with an exemplary embodiment.

Referring to FIG. 2, a block diagram of an imaging protocol manager 120 in operation is shown in accordance with certain examples. It should be understood that the devices/systems shown in FIG. 2 that work in conjunction with the imaging protocol manager 120 are for illustration not for limitation. The imaging protocol manager 120 can operate in conjunction with more, fewer, and/or different devices/systems. The imaging protocol manager 120 corresponds to the imaging protocol manager 120 in FIG. 1, which is a cloud-based software solution that helps maintain and standardize imaging protocols for equipment 230 (including CT scanner 232, MR scanner 234, X-ray acquisition system 236, for example) in a centralized way. An equipment service system 240 (e.g., GE Insite™, etc.), which facilitates services to equipment 230, can exchange equipment service information with the imaging protocol manager 120. One or more external application(s) 250 can leverage protocol information from the imaging protocol manager 120. For example, the external application(s) 250 may include an analytics application (e.g., GE Dose Watch™, etc.) that analyzes various parameters indicated in protocols.

As shown in FIG. 2, in some examples, the imaging protocol manager 120 includes an equipment registry 212, push/pull orchestrator 214, analytics engine 216, web host for protocol application 218, and various database including a protocol library 124. Version history of protocols can be maintained, events and activities for a protocol can be logged in the databases.

In operation, the equipment registry 212 registers imaging devices (e.g., CT scanner 232, MR scanner 234, X-ray acquisition system 236) with the protocol manager 120. The push/pull orchestrator 214 coordinates pulling protocols from registered devices to the protocol library 124. In some examples, clinical instructions are also pulled from the imaging devices and stored in the protocol library 124. The web host for protocol application 218 supports, for example, a web-based portal/application for the protocol team(s) to access the imaging protocol manager 120 from a user device (e.g., user device 130 of FIG. 1). The protocol team(s) can view and edit the protocols stored in the library 124. Approved protocols are published in the library 124.

The analytics engine 216 can perform analysis regarding protocol compliance, equipment operation, protocol changes, and so on. For example, the analytics engine 216 can analyze deviations of protocols (e.g., device protocol versus device protocol, device protocol versus standard protocol, standard protocol versus standard protocol, etc.), and track revisions and changes of protocols. In some examples, the analytics engine 216 can further perform protocol utilization analysis, performance analysis, benchmarking, joint commission compliance analysis, customized analytics for one or more key performance indicators (KPIs), and so on. A radiology administrator of a hospital can leverage the analytics engine 216 to manage compliance and periodic reporting of protocol usage in a clinical practice, for example. A review module 220 is configured to review and standardize the imaging protocols stored in the library 124. Example interfaces of the review module 220 are depicted in at least FIGS. 4-13. An editing module 222 is configured to edit the protocols stored in the library 124. The example editing module may also be configured to allow creation of new protocols for addition to the library 124. Example interfaces of the editing module 220 are depicted in at least FIGS. 14-26.

Figure 3:
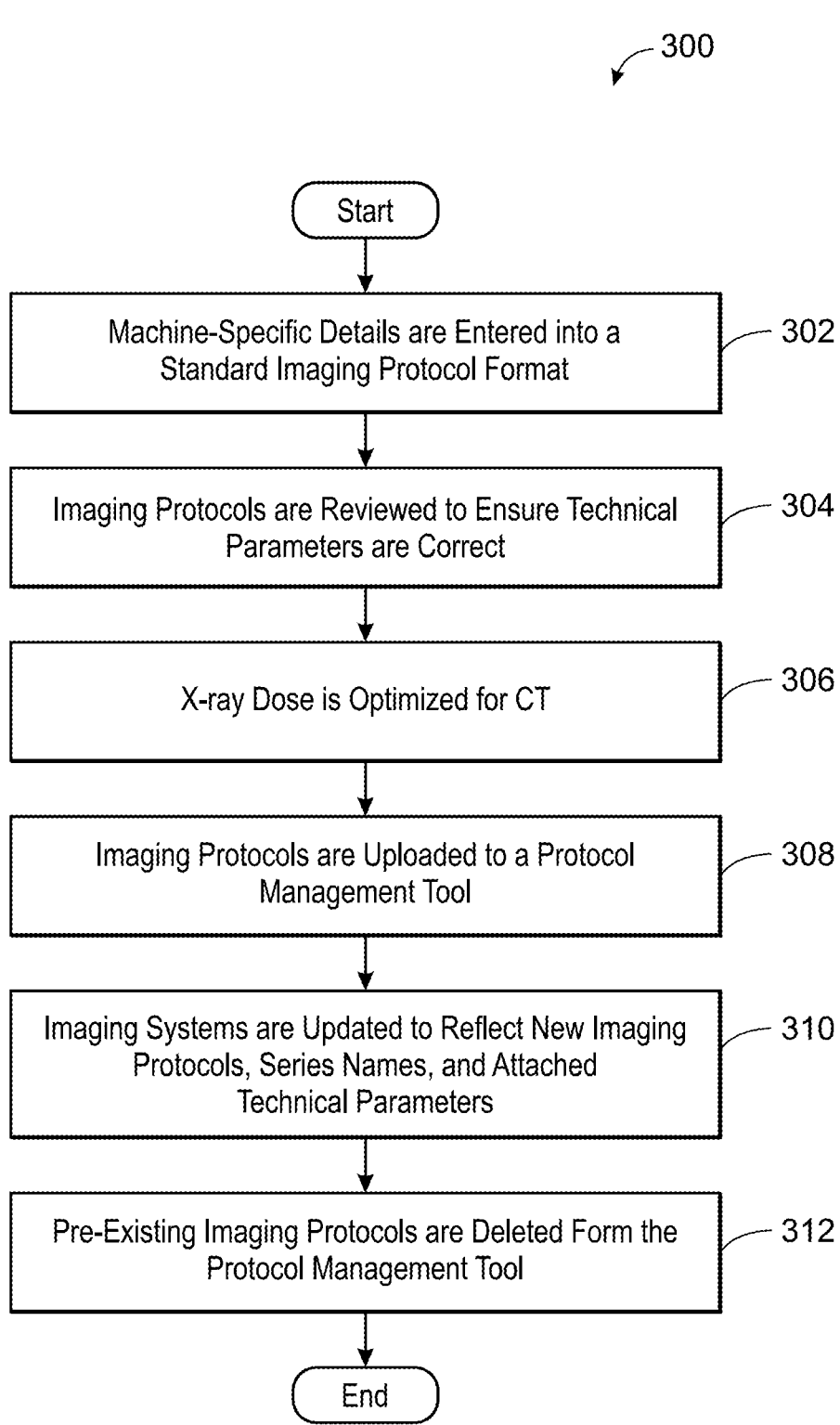
FIG. 3 is a method of standardizing the protocols in the imaging protocol manager.

FIG. 3 is a method 300 of standardizing the protocols in the imaging protocol manager. The method 300 begins at step 302 with machine-specific details being entered in a standard imaging protocol format. The machine-specific details may be entered into a user device 130 (e.g., a computer, an imaging machine terminal, etc.). In some examples, a lead CT or MR technologist enters the machine-specific details. At step 304, the imaging protocols are reviewed via the user device 130 to ensure the technical parameters of each imaging protocol are correct. In some examples, physicists review the imaging protocols. At step 306, an X-ray dose may be optimized. Specifically, the X-ray dose is optimized for protocols that will be carried out on CT machines. In some examples, the dose may be optimized by the external application 250 (e.g., GE Dose Watch™, etc.).

At step 308, the imaging protocols are uploaded to the protocol management tool. The protocols may be transferred from the user device 130 to the protocol manager 120 via a network connection. For example, when the user is using a web browser-based application on the user device 130 to enter or review protocol information, saving or approving the protocol may be sufficient to transfer the protocol to the protocol library 124 of the protocol manager 120. However, in other examples, the protocols may transfer at a designated time (e.g., a pre-determined time each day) or the user may have to select which protocols to transfer and use a transfer option on the web browser to transfer the protocols to the protocol manager 120. At step 310, imaging systems or scanning devices 112, 114, 116, 118 are automatically updated to reflect new imaging protocols, series names, and attached technical parameters. In some examples, the imaging systems 112, 114, 116, 118 automatically receive the updated or new protocols that are transferred to the protocol library 124. In some such examples, imaging systems 112, 114, 116, 118 may only be updated with relevant protocols. For example, a CT imaging system will only be updated with CT protocols. In other examples, technologists select which protocols from the protocol library 124 should be updated for each imaging system 112, 114, 116, 118. At step 312, pre-existing (e.g., outdated) imaging protocols are deleted from the library 124 of the protocol manager 120. In some examples, the pre-existing protocols are automatically removed (e.g., when a protocol is updated and a newer version exists, thus replacing the previous version). In other examples, the existing protocols are removed by a technologist. The method 300 is complete.

This disclosure provides an automated cloud-based imaging protocol review management system for the process. There are many technical and commercial advantages. For example, the solution is a cloud deployed solution and may scale easily to serve a large number of customers. Additionally, the solution is provided as a SaaS model and, in some examples, may be provided on a pay per use model. For example, the users may be charged on the actual usage hours of editing. This could be more cost-effective for some users. Further, the solution is web-based and may easily be accessed from anywhere over the internet using a browser.

Thus, the protocols can more easily be reviewed and edited, even when the user is not in the same physical location as the imaging device, or when a user is working remotely from the facilities.

The invention may be implemented on multi-modality imaging systems 112, 114, 116, 118, such as imaging system a CT imaging system, a magnetic resonance (MR) imaging system, a positron emission tomography (PET) imaging system, a single-photon emission CT (SPECT) imaging system, or an X-ray imaging system, and/or any other imaging modality including modalities yet to be developed, as well as combinations thereof (e.g., multi-modality imaging systems, such as PET/CT, PET/MR or SPECT/CT imaging systems.

The imaging systems 112, 114, 116, 118 are connected through an edge gateway to the cloud for IPM workflow. One or more imaging systems 112, 114, 116, 118 may be connected to the cloud via a back-office network, such as an edge services platform and further an edge agent runs on a gateway and/or other edge device that facilitates communication between an imaging system 112, 114, 116, 118 and the cloud. And the imaging systems 112, 114, 116, 118 are connected to an edge device which is connected to the cloud.

The IPM 120 is a cloud-based, multi-modality solution that provides access, insight, and governance to standardize imaging system protocols across an enterprise. From a core workflows standpoint, the IPM 120 pushes standard imaging protocols from the cloud to imaging systems 112, 114, 116, 118 registered with the protocol manager 120. The protocol manager 120 maintains a library 124 storing standard imaging protocols, determines whether an imaging system 112, 114, 116, 118 is compatible with the standard imaging protocol(s) to be pushed, creates a push command which requests pushing the standard imaging protocol(s) to a compatible imaging system, stores the push command in a command queue, converts the standard imaging protocol(s) to raw imaging protocol(s) usable by the imaging system. The imaging system polls the command queue to receive the push command, downloads the raw imaging protocol(s) from the protocol manage 120r, commits or refuses to commit the downloaded imaging protocol(s), and sends a notification to the protocol manager 120 indicating execution status of the push command.

The edge is a networking concept focused on bringing computing or processing as close to the source of data as possible in order to reduce latency and bandwidth use. Essentially, running fewer processes in the cloud and moving that processing (e.g., computing/storage) closer to the imaging system (e.g., via an edge server). And bringing computing or processing to the network's edge minimizes the amount of long-distance communication that has to happen between the Cloud and imaging system. Using an edge-deployed PaaS (e.g., GE Healthcare's Edison Edge Platform), we create microservices and orchestrations involved in IPM workflow.

Figures 4, 5:
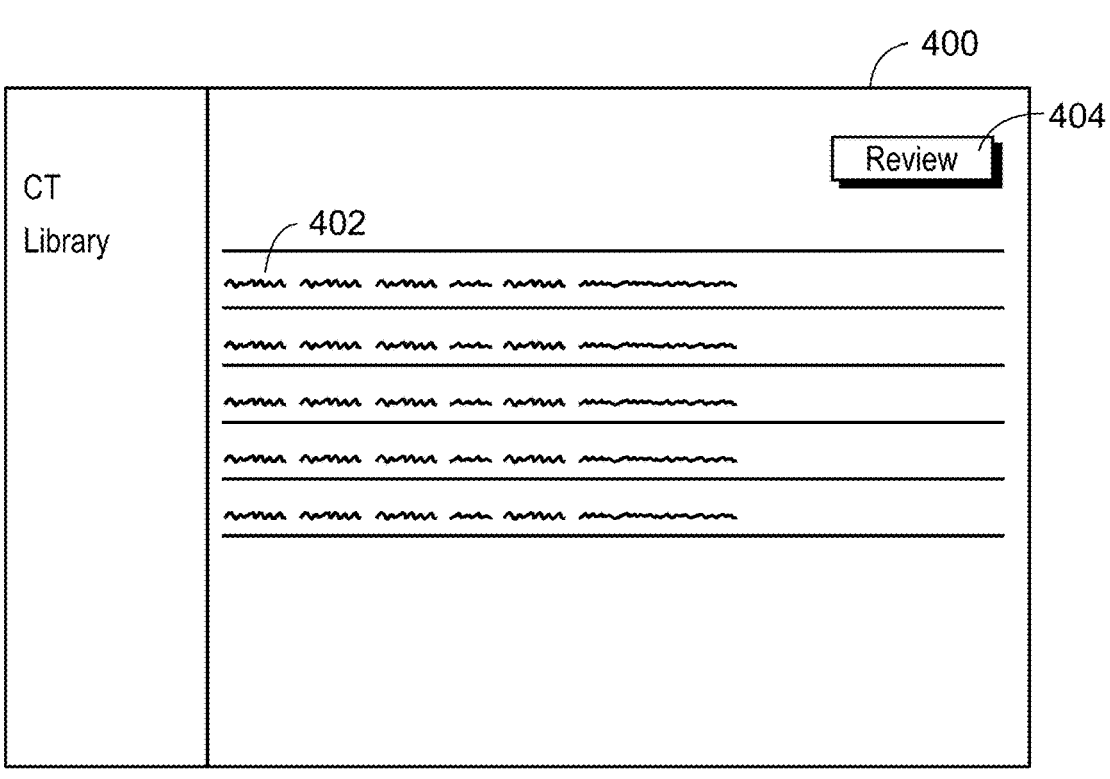

FIGS. 4-13 illustrate example embodiments of a review process of the imaging protocol manager 120. FIG. 4 depicts an example interface 400 on the user device that accesses the library 124 in the cloud storage of the protocol manager 120. The particular library is the CT library and displays protocols 402 that are appropriate for use with a CT imaging system. Other types of imaging systems may include separate libraries. To review the protocols 402, the user selects the "Review" button 404 on the interface 400. FIG. 5 depicts an example interface 500 that may be presented to the user after selecting "Review" 404 For example, the user or reviewer may be presented with a list of protocols 402 that need to be reviewed. Thus, a review status of each protocol may be "Not Reviewed." Additionally, if the protocol has been modified since the protocol was created, a date may be displayed under a "Last Modified" column. Finally, the interface 500 may indicate which CT machines have used a deviation of the standard protocol that is to be reviewed, shown in this example using a particular symbol identified in a key 502 at the bottom of the interface 500. In some examples, when reviewing the deviations of the standard protocol, the reviewer may prefer the deviation to the initial standard protocol and replace the initial standard protocol with the deviation. In some examples, the user may be able to select only the protocols assigned to the user by selecting "assigned to me" rather than "show all." Pull-down menus 504, 506 may also allow the user to select protocols within a certain review group name or model. A new review group can also be created. FIG. 6 depicts an interface 600 that may allow the user to create a new group. A review group may be desired so that a number of protocols 402 will be on a similar review schedule (e.g., scheduled for review every 365 days). Grouping the protocols 402 to be reviewed on a similar schedule can help ensure that the protocols 402 are being reviewed frequent enough for certain guidelines or regulations for accreditation (e.g., hospital guidelines, ACR guidelines, etc.). FIG. 7 depicts a selected group 702 of protocols 402 to be reviewed. The review can be initiated by selecting the menu icon 704 (e.g., in some examples, the menu icon may include three dots, a specific number of dots or dashes, etc.).

Figure 8:
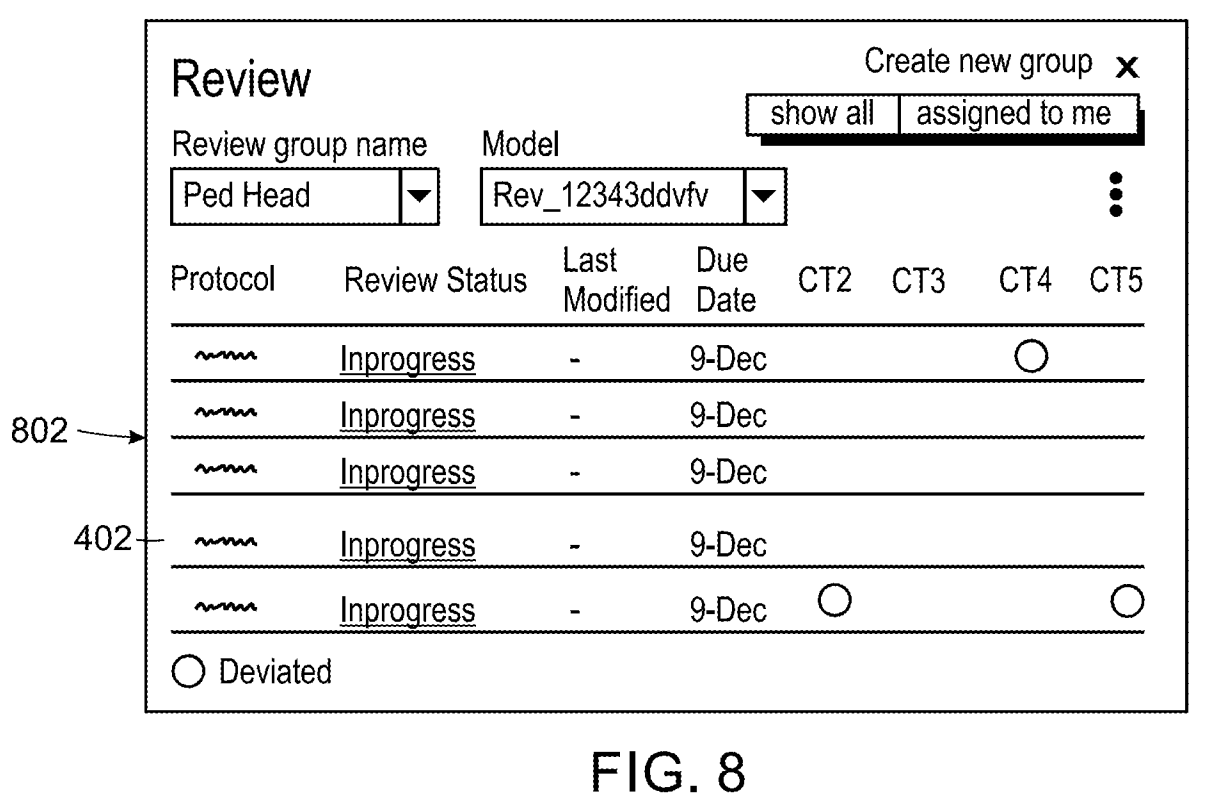
Figure 9:
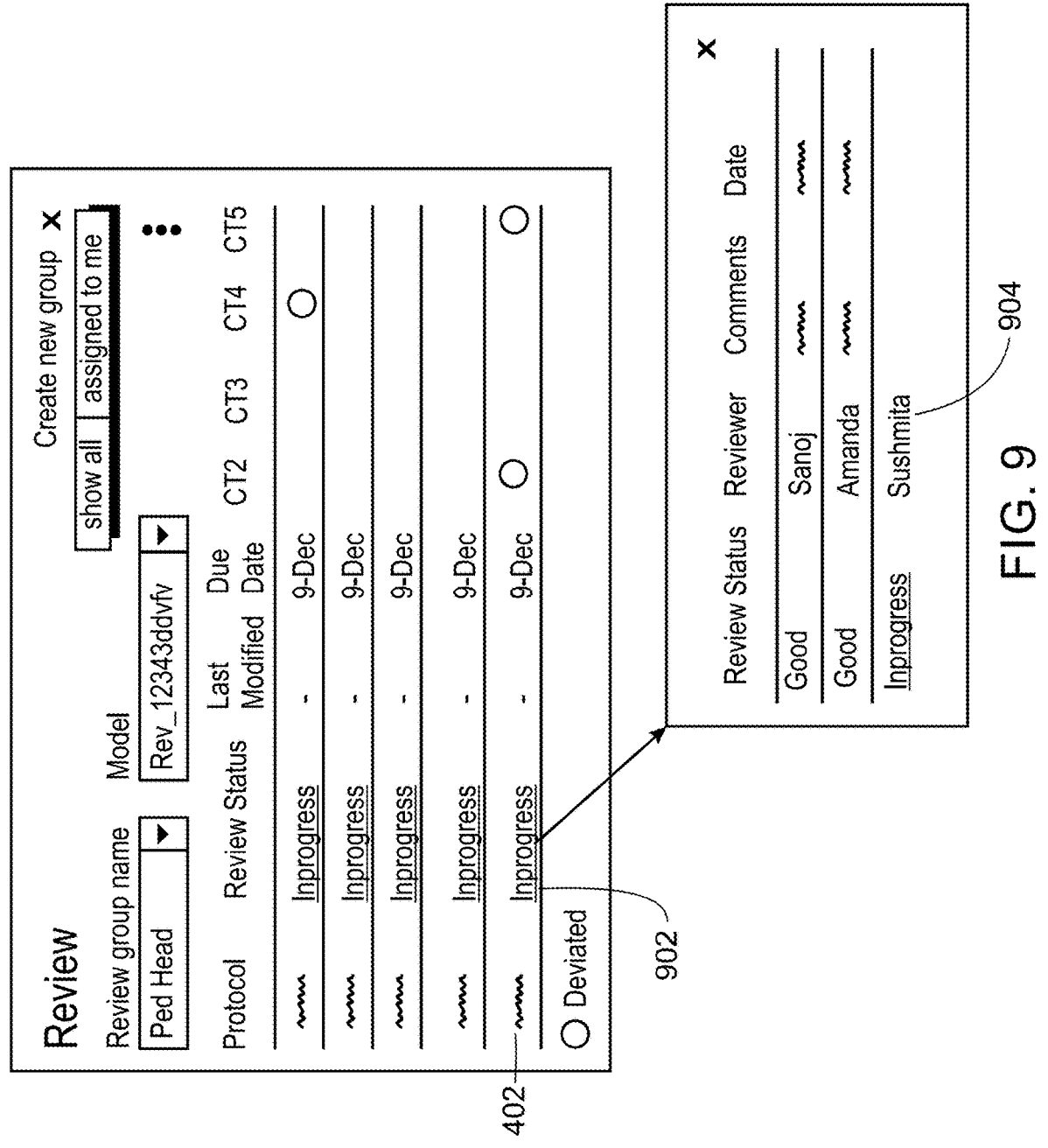

FIG. 8 depicts a group 802 of protocols 402 for which at least one designated reviewer has reviewed or initiated the review of the protocol 402. As shown in FIG. 9, selecting the hyperlink 902 "In progress" for a specific protocol 402 will show the user the designated reviewers 904 and the review status of each designated reviewer 904. In the illustrated example of FIG. 9, one of the reviewers 904 has not completed the review. Once all reviewers 904 have completed the review, as depicted in FIG. 10, the review status of the protocols 402 in the group will change to "Good." Additionally, the last modified date and the due date may be updated. The last modified date may be changed to the date of the final review, and the due date is changed according to the review schedule. For example, the group 802 may be reviewed every 90 days, so the due day is set for 90 days after the last modified date. Protocols may be reviewed periodically to ensure compliance with guidelines (e.g., hospital guidelines, accreditation guidelines, etc.), and/or to standardize the deviations of the protocols across all imaging systems. FIG. 11 depicts the group 802 when the due date for reviewing the protocols 402 is upcoming (e.g., within the next 10 days). The review status changes to "Due Soon" to notify the reviewer or user that the protocol reviewing date is upcoming.

Figure 12:
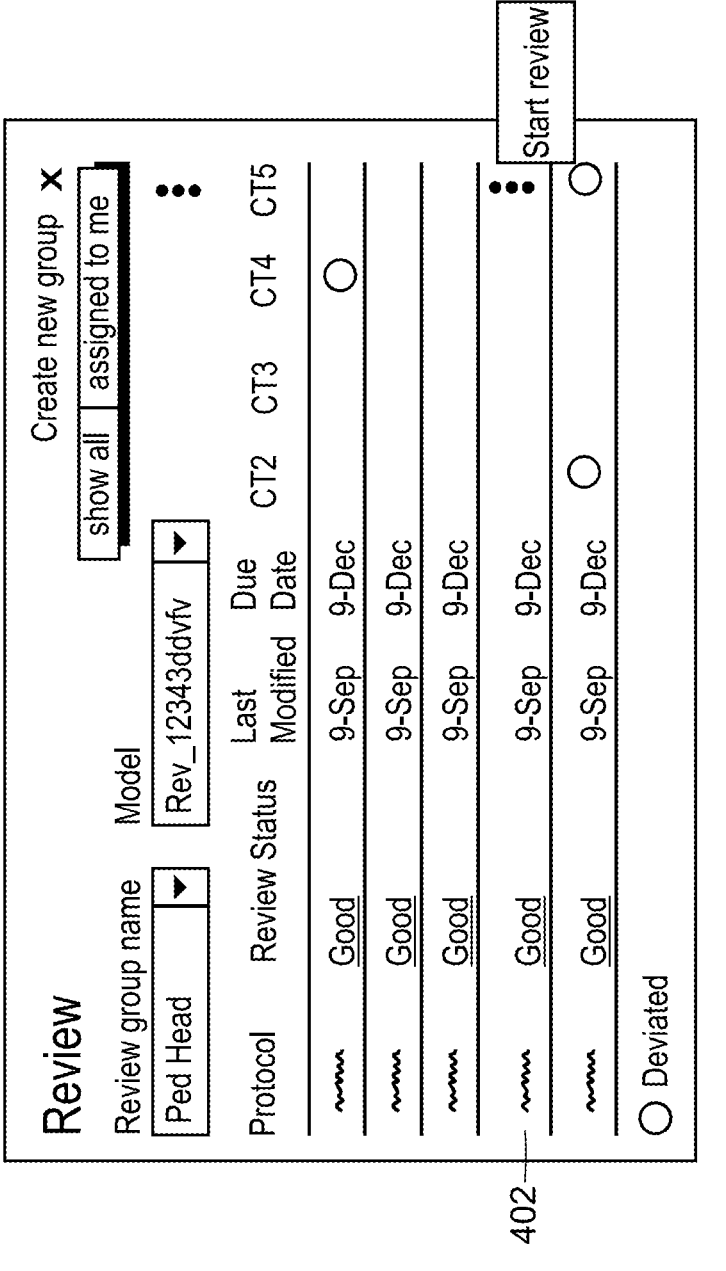
Figure 13:
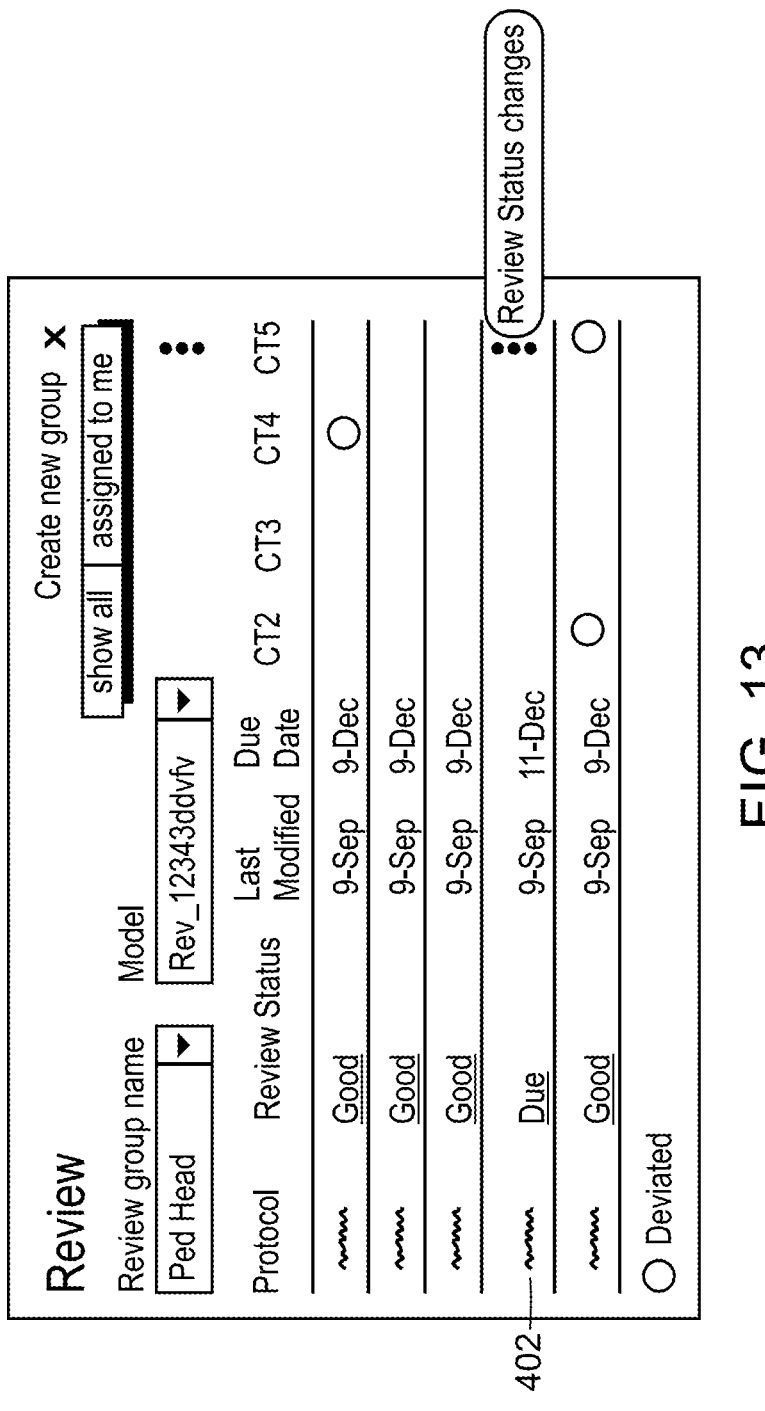

FIG. 12 depicts a user initiating a review on a protocol 402 where the status is "Good." That is, even when the review status is "Good" a user may review the protocol 402. Reviewing the protocol 402 affects the due date for the subsequent reviews. The status can then be changed to "Due," as depicted in FIG. 13.

Figures 14, 15:
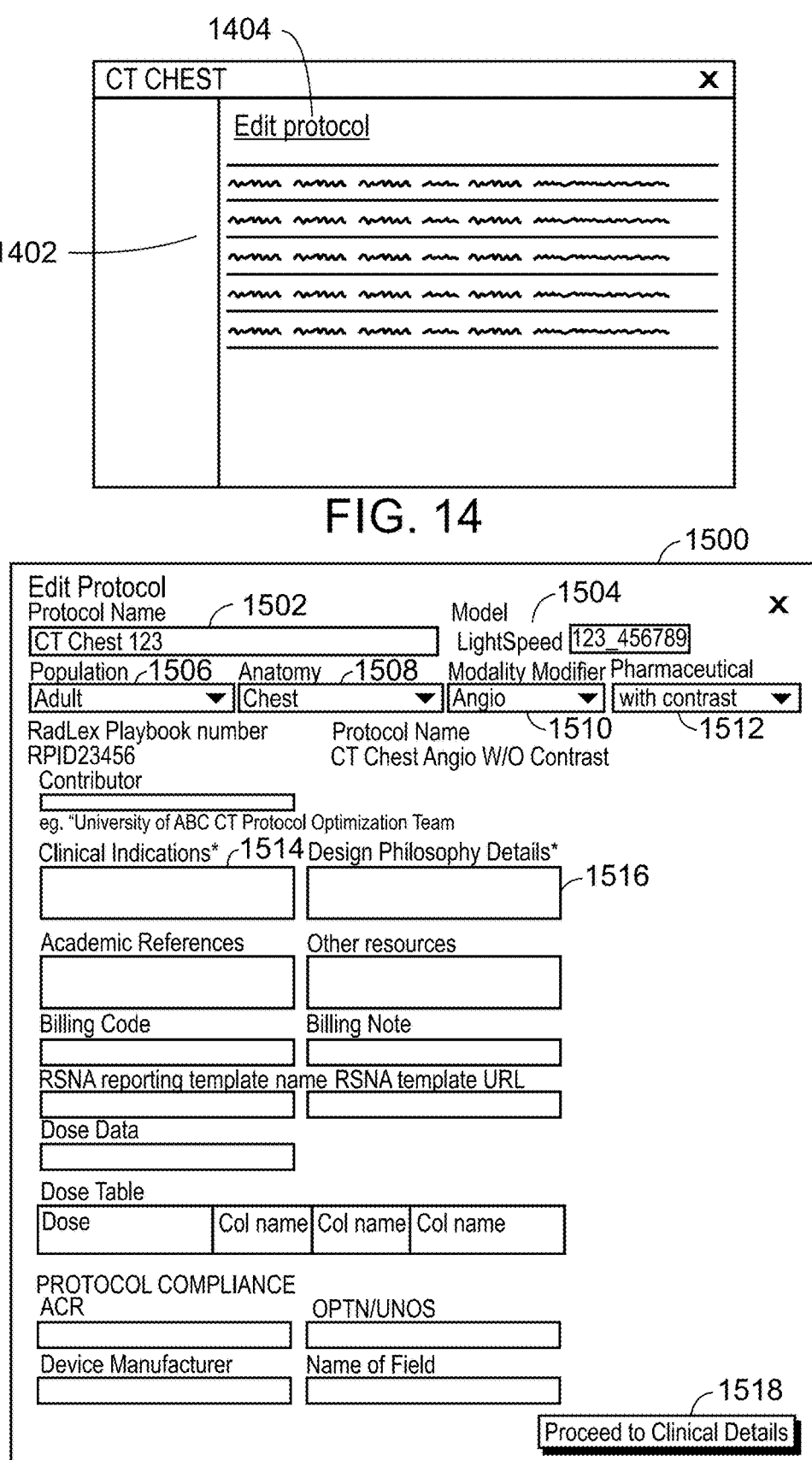
FIGS. 14-17 illustrate example embodiments of a protocol editing process of the imaging protocol manager.
Figure 16:
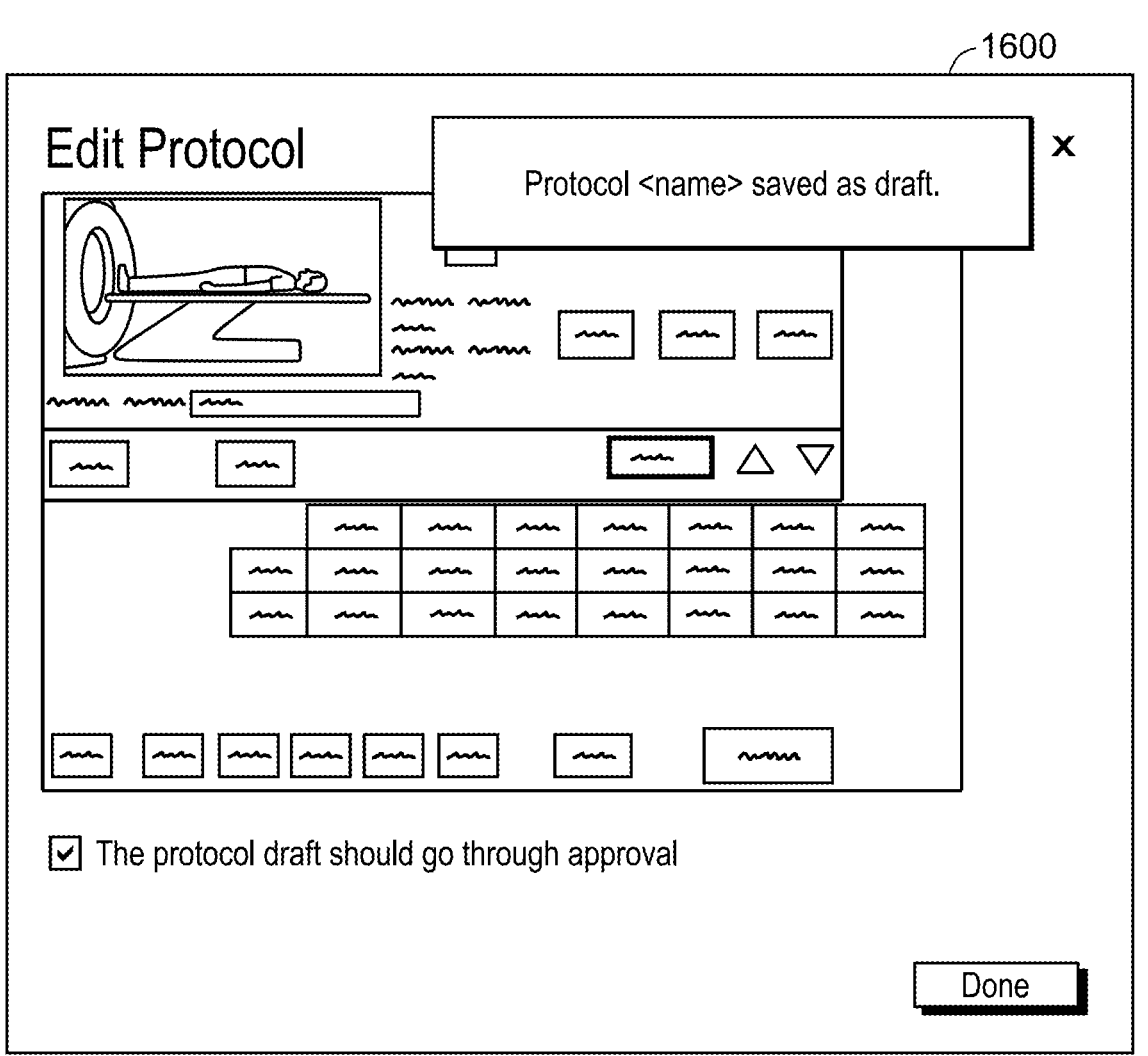
Figure 17:
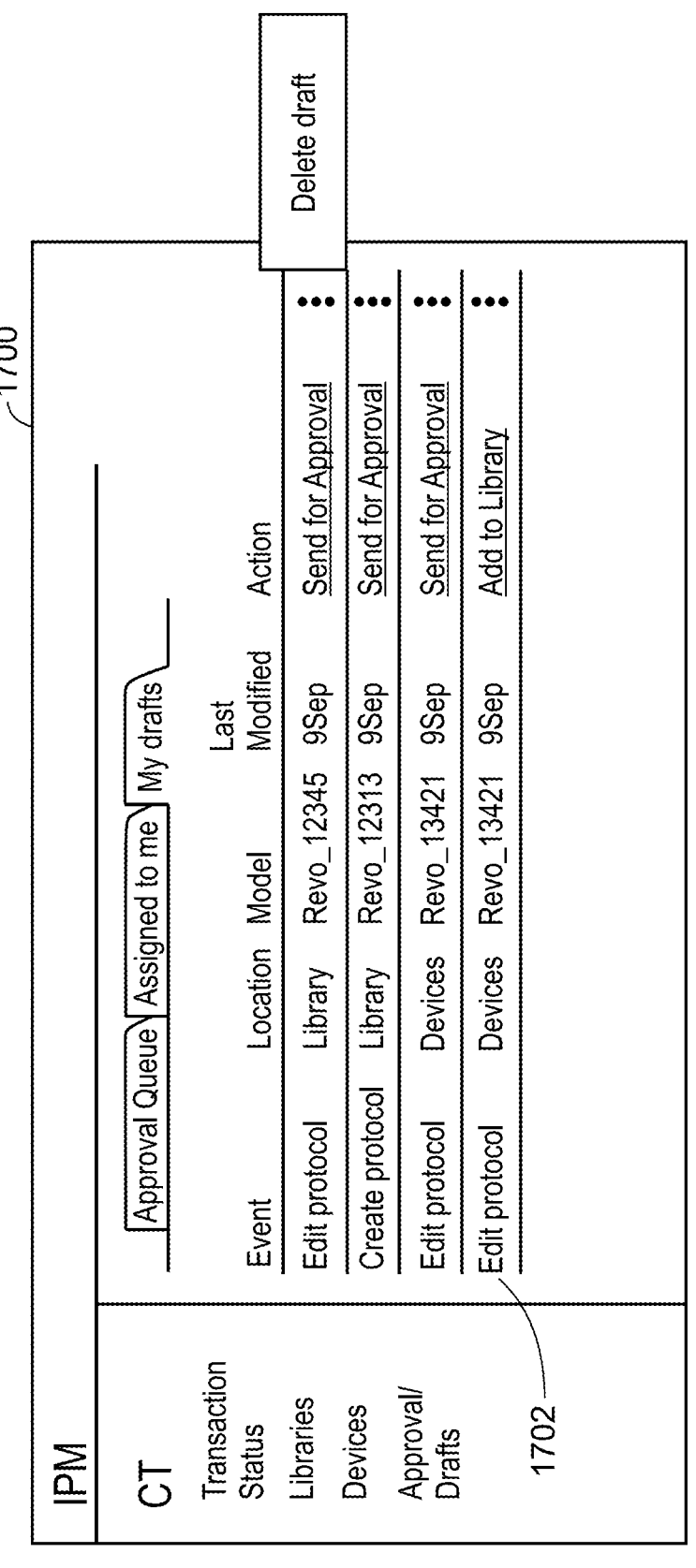

FIGS. 14-17 illustrate example embodiments of a protocol editing process of the imaging protocol manager 120. FIG. 14 depicts a list of protocols 1402 that are included in the CT protocol library. In the illustrated example, the CT protocols 1402 are specifically related to chest scans. A user can edit a protocol 1402 by selecting "edit protocol" 1404 FIG. 15 depicts an interface 1500 that allows the user to edit the protocol information. The user can enter information in any of the data fields, but is required to enter information in certain fields, such as protocol name 1502, model 1504, population 1506, anatomy 1508, modality modifier 1510, pharmaceutical 1512, clinical indications 1514, and design philosophy details 1516. After the user has completed editing the protocol 1402 or entering information in the data fields, the user can select "proceed to editing clinical details" 1518. FIG. 16 depicts an example simulated interface 1600 that allows the user to update the clinical details or instructions. The simulated interface 1600 matches what would be displayed to a user on a terminal of an imaging system. Thus, the user can update the clinical details of the protocol 1402 without requiring down-time for the imaging system 112, 114, 116, 118 because the user can update the clinical details via the web browser platform. When the user is finished updating the clinical details, the user can select whether the protocol draft should go through approval before being added to the protocol library. FIG. 17 depicts an interface that lists the different protocol drafts 1702 that are ready to send for approval or are ready to add to library 124. A protocol draft 1702 may be ready to add to the library 124 if the user did not indicate the protocol draft 1702 needs approval after editing the protocol, or after the edited protocol has been approved. The user can also choose to delete the protocol draft 1702 in the draft protocol interface 1700.

FIGS. 18-26 illustrate example embodiments of a process to add a protocol from a device to the library of the imaging protocol manager. FIG. 18 depicts a list 1802 of protocols 1804 that may exist on one or more devices. For example, a technologist may have created or edited clinical details of a protocol on an imaging system. The user can select the protocols 1802 to be added to the library 124. After selecting the protocols to be added to the library 124, a list of duplicates 1902 may be presented to the user, as depicted in FIG. 19. The user can then add comments 2002 for each duplicate protocol 1902 being added to the library 124, as shown in FIG. 20. The comments 2002 may include a description of why the protocol was used, or what was changed if the protocol is a duplicate. The user can also select whether the protocol 1902 will go through an approval process before being added to the library 124. A user notification 2102 may be displayed to the user that the protocols 1902 are sent for approval, as indicated in FIG. 21.

FIG. 22 depicts the list 2202 of protocols 2204 that are pending approval. The event may indicate why the protocol 2204 is pending approval. For example, if the event is "add to library" the protocol 2204 may have been added from a device (e.g., an imaging system 112, 114, 116, 118). A new protocol may have an event label of "create protocol" and an edited protocol may have an event label of "edit protocol." The user can select the pending hyperlink 2206 on each protocol to see the approval status and comments 2304 from each reviewer 2302, as shown in FIG. 23. FIG. 24 depicts an interface 2400 to add comments to a protocol that has been added to a library to resolve duplicate or slot (e.g., storage location) issues. FIGS. 25 and 26 depict an example protocol 2502 that has been rejected by the reviewers. The user can view the comments from the reviewers by selecting the "see comments" button 2602 on the add to library interface 2600 of FIG. 26. The user may then edit the protocol 2502 based on the comments and resubmit the protocol 2502 for approval.

FIGS. 27-29 illustrate example embodiments of a process rename a protocol 2702 in the imaging protocol manager. In the list of protocols 2702 in the libraries section of the protocol manager, the user may rename a protocol 2702. The user may also select whether the renamed protocol should go through an approval, as shown in a secondary interface 2704 of FIG. 27. The user can then change the protocol name 2802, and save or chancel the name change, as shown in FIG. 28. If the user saves the name change, and has selected the protocol to go through the approval process after the name change, the user may receive a notification 2902 that the rename has gone for approval, as depicted in FIG. 29. If the user did not select the protocol to go through the approval process, the new name of the protocol will be displayed.

Figure 31:
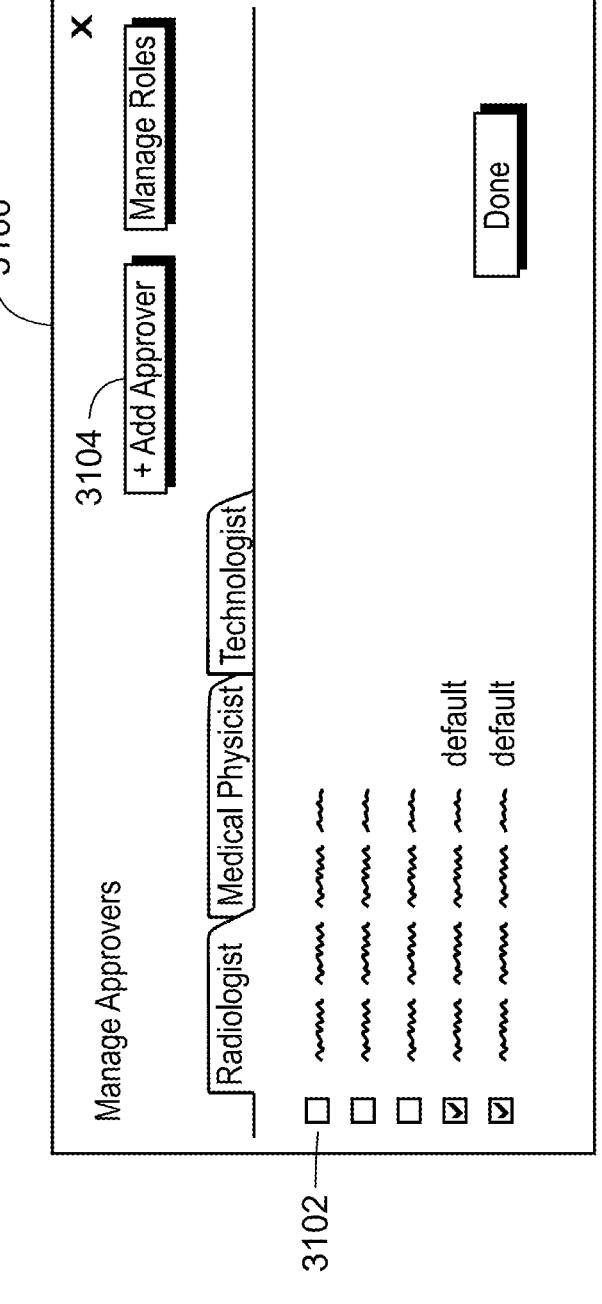

FIGS. 30-31 illustrate example embodiments of a process to manage approvers of the imaging protocol manager. In some examples, the user is able to manage who is reviewing a draft protocol for approval. For example, administrators may have access to an interface 3000 for managing approvers or reviewers 3102. FIG. 30 depicts a list of drafts that are awaiting approval. The user can select the manage approvers button 3002 to add or remove approvers. FIG. 31 depicts an example interface 3100 that allows the user to manage the approvers 3102. Approvers 3102 may be sorted by role (e.g., radiologist, medical physicist, technologist, etc.) An approver 3102 can be added by selecting the "+Add approver" button 3104. A name may then be added to the list. Additionally, if the approver's name is listed but not selected, the person may be added as an approver by simply selecting their name (e.g., checking the box). The role of each approver may also be managed in this interface.

Thus, certain examples provide protocol management systems and methods including registering devices, organizing and editing protocols in the cloud using a web-based application, and pushing protocols into the device(s) for use. Certain examples facilitate protocol organization to define one protocol with an association with multiple scanners and having instructions/parameters that are different for different scanners/devices. Devices can be baselined, and protocol can be standardized, organized, and managed with respect to device content.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, including best mode, it will be apparent to those of ordinary skill in the art that numerous modifications, including, but not limited to, form, function, manner of operation and use may be made without departing from the principles and concepts set forth herein in this written description. Also, as used herein, the examples and embodiments, in all respects, are meant to be illustrative only and should not be construed to be limiting in any manner.

13

14

What is claimed is:

1. A system comprising:

one or more processors and one or more storage devices in a cloud;

a cloud-based imaging protocol manager leveraging the one or more processors and the one or more storage devices, the imaging protocol manager comprising:

a library storing imaging protocols; and wherein the one or more processors review and standardize the imaging protocols stored in the library, wherein the one or more processors are further configured to assign the imaging protocols to one or more review groups, each review group having a predefined review schedule, to automatically calculate a review due date for each imaging protocol based on the review schedule, to assign a plurality of reviewers to each imaging protocol, to track review status for each reviewer independently via a web browser-based application, and to prevent publication of an imaging protocol to the library until all assigned reviewers have completed review and approval;

a user interface device includes the web browser-based application to access imaging protocols stored in the library, the web browser-based application to enable creation, editing, and review of the imaging protocols stored in the library, wherein the imaging protocols are approved using the web browser-based application prior to being published in the library; and a plurality of imaging systems, wherein the plurality of imaging systems accesses the imaging protocols from the library.

2. The cloud-based imaging protocol manager of claim 1, wherein the web browser-based application is accessible using any device having a web browser.

3. The cloud-based imaging protocol manager of claim 1, wherein the web browser-based application enables management of the imaging protocols without interrupting service of the imaging systems.

4. The cloud-based imaging protocol manager of claim 1, wherein the web browser-based application includes a simulated interface similar to a terminal of an imaging system.

5. The cloud-based imaging protocol manager of claim 4, wherein editing the imaging protocols stored in the library includes editing clinical details using the simulated interface.

6. The cloud-based imaging protocol manager of claim 1, wherein reviewing the imaging protocols includes creating groups of imaging protocols to be reviewed on a similar schedule.

7. The cloud-based imaging protocol manager of claim 6, further comprising setting the review schedule of the imaging protocols according to regulations for accreditation.

8. The cloud-based imaging protocol manager of claim 1, wherein editing the imaging protocols includes obtaining approval of the edited imaging protocols before the imaging protocols are added to the library.

9. A method performed by an imaging protocol manager in a cloud for reviewing imaging protocols, the method comprising:

storing imaging protocols in the cloud;

acquiring machine-specific details in a standard imaging protocol format;

reviewing imaging protocols, using one or more processors and a web browser-based application, wherein the one or more processors are further configured to assign the imaging protocols to one or more review groups, each review group having a predefined review schedule, to automatically calculate a review due date for each imaging protocol based on the review schedule, to assign a plurality of reviewers to each imaging protocol, to track review status for each reviewer independently via a web browser-based application, and to prevent publication of an imaging protocol to the library until all assigned reviewers have completed review and approval;

uploading imaging protocols to a cloud-based imaging protocol manager; and updating imaging systems with the uploaded imaging protocols.

10. The method of claim 9, wherein reviewing imaging protocols includes editing imaging protocols.

11. The method of claim 10, wherein reviewing imaging protocols includes approving edited imaging protocols.

12. The method of claim 10, wherein uploading imaging protocols includes uploading approved imaging protocols.

13. The method of claim 10, wherein editing imaging protocols includes editing clinical details using a simulated interface.

14. The method of claim 9, further including optimizing X-ray dose for CT imaging protocols.

15. The method of claim 9, further including deleting pre-existing imaging protocols from the imaging protocol manager.

16. A system comprising:

one or more processors and one or more storage devices in a cloud;

a cloud-based imaging protocol manager leveraging the one or more processors and the one or more storage devices, the imaging protocol manager comprising:

a library storing imaging protocols;

wherein the one or more processors review and standardize the imaging protocols stored in the library, wherein the one or more processors are further configured to assign imaging protocols to one or more review groups, each review group having a predefined review schedule, to automatically calculate a review due date for each imaging protocol based on the review schedule, to assign a plurality of reviewers to each imaging protocol, to track review status for each reviewer independently via a web browser-based application, and to prevent publication of an imaging protocol to the library until all assigned reviewers have completed review and approval; and edit the imaging protocols stored in the library;

a user interface device includes the web browser-based application to access imaging protocols stored in the library, the web browser-based application to enable creation, editing, and review of the imaging protocols stored in the library, wherein the imaging protocols are approved using the web browser-based application prior to being published in the library; and a plurality of imaging systems, wherein the plurality of imaging systems accesses the imaging protocols from the library.

17. The cloud-based imaging protocol manager of claim 16, wherein the web browser-based application is accessible using any device having a web browser.

18. The cloud-based imaging protocol manager of claim 16, wherein the web browser-based application enables management of the imaging protocols without interrupting service of the imaging systems.

19. The cloud-based imaging protocol manager of claim 16, wherein the web browser-based application includes a simulated interface similar to a terminal of an imaging system.

20. A method performed by an imaging protocol manager in a cloud for reviewing imaging protocols, the method comprising:

storing imaging protocols in the cloud;

acquiring machine-specific details in a standard imaging protocol format;

reviewing imaging protocols, via one or more processors and a web browser-based application, wherein the one or more processors are further configured to assign imaging protocols to one or more review groups, each review group having a predefined review schedule, to automatically calculate a review due date for each imaging protocol based on the review schedule, to assign a plurality of reviewers to each imaging protocol, to track review status for each reviewer independently via a web browser-based application, and to prevent publication of an imaging protocol to the library until all assigned reviewers have completed review and approval;

editing imaging protocols, via the one or more processors, in a web browser-based application;

uploading imaging protocols to a cloud-based imaging protocol manager;

updating imaging systems with the uploaded imaging protocols.

* * * * *